United States Patent
Zhang et al.

(10) Patent No.: US 9,700,581 B2
(45) Date of Patent: Jul. 11, 2017

(54) URINE STEM CELLS FOR SKELETAL MUSCLE GENERATION AND USES THEREOF

(71) Applicant: Wake Forest University Health Sciences, Winston-Salem, NC (US)

(72) Inventors: Yuanyuan Zhang, Winston-Salem, NC (US); Emmanuel C. Opara, Durham, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 14/427,150

(22) PCT Filed: Sep. 10, 2013

(86) PCT No.: PCT/US2013/058955
§ 371 (c)(1),
(2) Date: Mar. 10, 2015

(87) PCT Pub. No.: WO2014/040030
PCT Pub. Date: Mar. 13, 2014

(65) Prior Publication Data
US 2015/0238531 A1    Aug. 27, 2015

Related U.S. Application Data

(60) Provisional application No. 61/699,056, filed on Sep. 10, 2012.

(51) Int. Cl.
*A61K 35/22*    (2015.01)
*A61K 38/18*    (2006.01)
*C12N 5/0775*   (2010.01)
*C12N 5/071*    (2010.01)
*A61K 9/00*     (2006.01)
*A61K 9/16*     (2006.01)
*A61K 35/545*   (2015.01)

(52) U.S. Cl.
CPC ............ *A61K 35/22* (2013.01); *A61K 9/0019* (2013.01); *A61K 9/16* (2013.01); *A61K 38/18* (2013.01); *A61K 38/185* (2013.01); *A61K 38/1825* (2013.01); *A61K 38/1833* (2013.01); *A61K 38/1858* (2013.01); *A61K 38/1866* (2013.01); *C12N 5/069* (2013.01); *C12N 5/0668* (2013.01); *C12N 5/0684* (2013.01); *C12N 5/0685* (2013.01); *A61K 35/545* (2013.01); *C12N 2501/165* (2013.01); *C12N 2506/1392* (2013.01); *C12N 2506/25* (2013.01)

(58) Field of Classification Search
CPC ................ A61K 35/22; A61K 38/1858; A61K 38/1866; A61K 38/1833; A61K 38/1825; A61K 38/185; A61K 38/18; C12N 5/0668; C12N 5/0684
See application file for complete search history.

(56) References Cited

U.S. PATENT DOCUMENTS

2010/0111914 A1   5/2010   Zhang et al.
2011/0059052 A1   3/2011   Ra et al.

FOREIGN PATENT DOCUMENTS

EP          2075002 B1      2/2013
WO    WO 2010/065239 A1    6/2010

OTHER PUBLICATIONS

Extended European Search Report, EP 13835201.8, mailed Mar. 21, 2016.
Wu S et al. Implantation of autologous urine derived stem cells expressing vascular endothelial growth factor for potential use in genitourinary reconstruction. The Journal of Urology. Aug. 2011; 186: 640-647.
Liu G et al. Skeletal myogenic differentiation of urine-derived stem cells and angiogenesis using microbeads loaded with growth factors. Biomaterials. Jan. 2013; 34(4): 1311-1326.
International Search Report and Written Opinion, PCT/US2013/058955, mailed Dec. 20, 2013.
Zhao W et al. Periurethral injection of autologous adipose-derived stem cells with controlled-release nerve growth factor for the treatment of stress urinary incontinence in a rat model. European Urology. Jan. 2011; 59(1): 155-163.

*Primary Examiner* — Daniel C Gamett
(74) *Attorney, Agent, or Firm* — Myers Bigel, P.A.

(57) ABSTRACT

Provided herein are methods of treating a subject in need of treatment for a urological condition including administering urine stem cells to said subject in a treatment effective amount; and, in conjunction therewith, administering growth factors to said subject in an amount effective to promote differentiation of said stem cells into skeletal muscle cells. Compositions useful for the same are also provided.

13 Claims, 21 Drawing Sheets

US 9,700,581 B2

URINE STEM CELLS FOR SKELETAL MUSCLE GENERATION AND USES THEREOF

STATEMENT OF GOVERNMENT SUPPORT

This invention was made in part with government support under grant R01DK080897 awarded by the NIH. The government has certain rights in the invention.

FIELD OF THE INVENTION

This invention relates generally to the isolation of stem cells from urine, cells isolated, differentiation thereof into multiple lineages, and methods of use of the same.

BACKGROUND OF THE INVENTION

Regenerative medicine is an applied field of tissue engineering that focuses on the regeneration of damaged tissues of the body. Applications of regenerative medicine include the reconstruction or replacement of organs and other tissues. However, a donor shortage limits the supply of viable cells to use for these applications. More alternative sources of cells are needed, as well and improved strategies for their use and administration.

SUMMARY OF THE INVENTION

Provided herein are methods of treating a subject in need of treatment for a urological condition (e.g., stress urinary incontinence (UI) or vesicoureteral reflux (VCR)), including administering urine stem cells to said subject in a treatment effective amount; and, in conjunction therewith, administering growth factors to said subject in an amount effective to promote differentiation of said stem cells into skeletal muscle cells.

In some embodiments, the administering is carried out by administering the cells to the urethra of the subject (e.g., into a sphincter muscle tissue). In some embodiments, the administering is carried out by injection.

In some embodiments, the growth factors are provided in a polymeric matrix. In some embodiments, the growth factors are provided in polymeric microspheres. In some embodiments, the polymeric microspheres comprise alginate.

In some embodiments, the growth factors comprise an angiogenic growth factor, a skeletal myogenic growth factor, and/or a neurogenic growth factor. In some embodiments, the growth factors comprise one or more growth factors selected from the group consisting of: VEGF, IGF-1, FGF-1, PDGF, HGF and NGF.

In some embodiments, the growth factors are released over a period of from 2 to 6 weeks (e.g., about 4 weeks).

In some embodiments, the cells are provided in a pharmaceutically acceptable carrier. In some embodiments, the carrier comprises a collagen gel, a hydrogel, a temperature sensitive gel or a hyaluronic acid gel.

In some embodiments, the administering is carried out by simultaneous administration of said cells and said growth factors. In some embodiments, the cells and said growth factors are provided in the same composition for said administering.

Further provided are compositions for use in the treatments as described herein.

BRIEF DESCRIPTION OF THE DRAWINGS

FIG. 3A) Gross morphology of the implants showing details of vascularization and implant size. Neovascularization of grafts was observed in G9 and G10 compared to the poor vascularization of the G1 grafts (Gel alone+ empty beads). FIG. 3B) Weight changes among implanted grafts after 4 weeks in vivo. *$p<0.05$, **$p<0.01$. FIG. 3C) Histochemical analyses of implanted grafts after 4 weeks in vivo. Masson's Trichrome staining on the grafts depicts cells (red) more abundant in G9 and G10. FIG. 3D) Implanted cells were detected in vivo by immunofluorescent labeling using human specific nuclear mitotic apparatus antibody (right upper corner), stained in red. Specific staining appears reddish-purple (arrows) due to colocalization with DAPI (blue) stained nucleus. Scale bar=50 µm. FIG. 3E) Semi-quantitative analyses human nuclei/DAPI staining ratio in implanted grafts.

FIG. 5D) with Human nuclei specific marker. Specific staining (shown by arrows) appears green with nuclear staining in red (human nuclei) and blue (DAPI) indicating these were implanted cells that successfully differentiated to endothelial cells in vivo. Scale bar=50 µm.

DETAILED DESCRIPTION OF THE PREFERRED EMBODIMENTS

Figure 1:
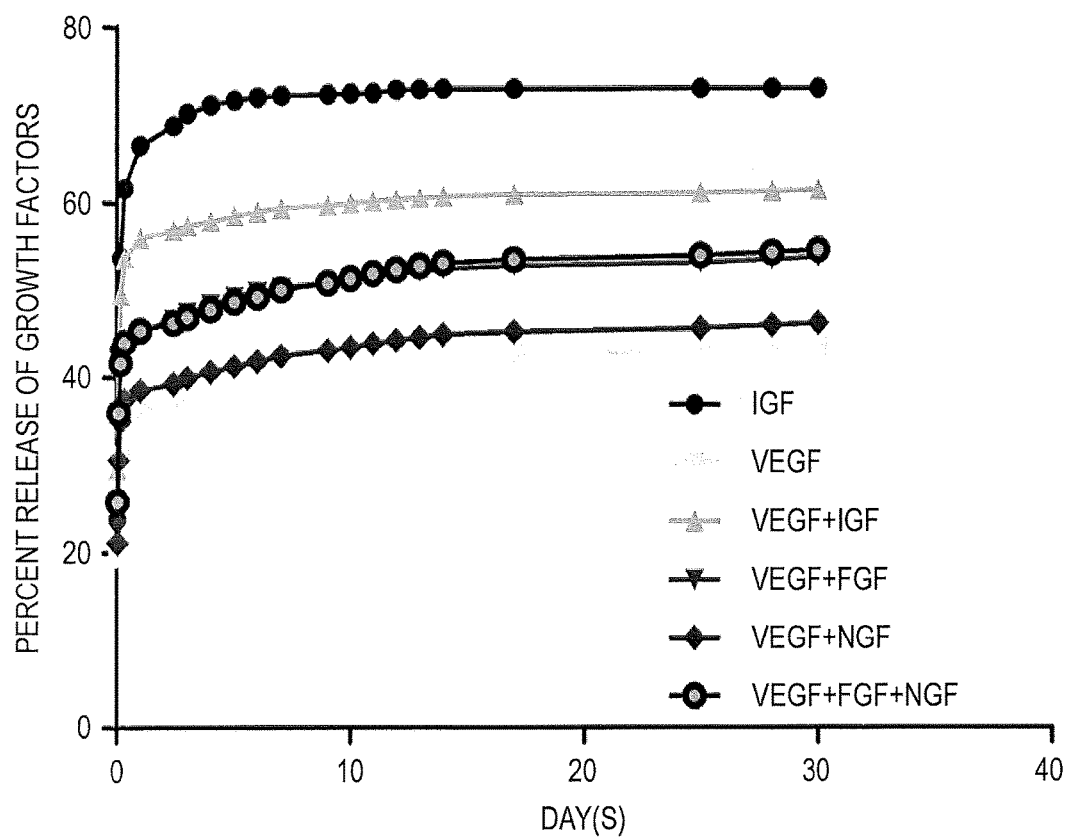
FIG. 1 Controllable release curve of alginate beads in vitro. The microbeads loaded growth factors, including I-125 radio-labeled VEGF, IGF and unlabeled FGF-1, NGF, were released quickly in the first few days after overnight incubation, regardless of the radiolabel. When two or more growth factors were incorporated, no significant change in the release kinetics was seen.

The present invention concerns stem cells from urine and their use for tissue engineering. Advantageously, cells found in urine may be obtained without the need for a tissue biopsy, preventing discomfort and possible complications associated with the harvest of cells.

The disclosures of all cited United States Patent references are hereby incorporated by reference to the extent that they are consistent with the disclosures herein. As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" and "/" refer to and encompass any and all possible combinations of one or more of the associated listed items, as well as the lack of combinations when interpreted in the alternative ("or").

"Urine stem cells" or "USC" are cells normally found in, and collected and/or isolated from, urine, which cells as disclosed herein possess both pluripotency and proliferative potential. A USC is "pluripotent" in that it is capable of giving rise to various cell types within one or more lineages. For example, USC according to some embodiments possess the potential to differentiate into one or more of the following: bladder urothelial, smooth muscle, endothelium, interstitial cells, and even bone, muscle, epithelial cells and other types of cells and tissues (e.g., fat, cartilage, nerve).

In some embodiments USC will double upon growing between 24-48 hours (e.g., every 31.3 hours), allowing them to be grown in large quantities. In further embodiments, USC do not induce tumor formation (as compared to embryonic stem cells), and in some embodiments USC do not require feeder cells for growth or differentiation.

"Isolated" signifies that the cells are placed into conditions other than their natural environment. However, the term "isolated" does not preclude the later use of these cells thereafter in combinations or mixtures with other cells.

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric. In some embodiments, subjects are from 0-5 years old, from 6-15 years old, from 16-25 years old, from 26-45 years old, and/or from 46-65 years old and even from above 65 years old.

Subjects may also include animal subjects, particularly mammalian subjects such as canines, felines, bovines, caprines, equines, ovines, porcines, rodents (e.g., rats and mice), lagomorphs, primates (including non-human primates), etc., for e.g., veterinary medicine and/or pharmaceutical drug development purposes.

1. Collection of Cells.

Urine stem cells may be collected from any animal that produces urine, including humans. In some embodiments of the present invention, urine stem cells are collected from the urine of a mammal. For example, USC may be collected from the urine of a dog, cat, pig, cow, horse, monkey or human. In particular embodiments, urine stem cells are obtained from the urine of a human.

Urine stem cells may be collected from any portion of the urinary tract. In some embodiments, USC are collected from the upper urinary tract (UUT) (kidneys, ureter), e.g., via a catheter such as a nephrostomy catheter. In other embodiments, USC are collected from the lower urinary tract (bladder, urethra), via a catheter such as a urinary catheter.

In some embodiments, USC are collected from samples of fresh spontaneous urine, or drainage urine through a urethral catheter or from a bladder wash. Urine samples can be centrifuged at 1500 RPM for 5 minutes at 4° C., the supernatant aspirated and cells washed with a suitable solution such as phosphate-buffered saline (PBS). The PBS may optionally contain serum such as 5% fetal bovine serum (FBS), and/or an antibiotic such as 1% penicillin-streptomycin to protect cells from injury and potential infection, respectively.

Further examples of methods and apparatuses for isolating cells from biological fluids may be found in, e.g., U.S. Pat. No. 5,912,116; U.S. Patent Application No. 20040087017; U.S. Patent Application No. 20020012953; and WO 2005/047529.

2. Selection and Propagation of Cells.

In some embodiments, collected USC are expanded. "Expanding" refers to an increase in number of viable cells. Expanding may be accomplished by, e.g., growing the cells through one or more cell cycles wherein at least a portion of the cells divide to produce additional cells.

The "primary culture" is the first culture to become established after seeding collected cells into a culture vessel. "Passaging" refers to the transfer or subculture of a culture to a second culture vessel, usually implying mechanical or enzymatic disaggregation, reseeding, and often division into two or more daughter cultures, depending upon the rate of proliferation. If the population is selected for a particular genotype or phenotype, the culture becomes a "cell strain" upon subculture, i.e., the culture is homogeneous and possesses desirable characteristics. The establishment of "cell lines," as opposed to cell strains, are by and large undifferentiated, though they may be committed to a particular lineage.

USC according to some embodiments may be passaged from 0, 1 or 2 to 5, 6, 7, 8, 9, 10, 11 or 12 times. In some embodiments, USC are passaged before use at least 2, 3, 4, 5, or 6 times, up to 7, 8, 9, 10, 11 or 12 times. In some embodiments, one USC clone can generate $64\times10^6$ cells at passage 4 in 4 weeks. According to some embodiments, at least $10^9$ cells at the early passage (<p5) may be generated from 3 or 4 urine samples in 6-7 weeks.

"Selection" can be based upon any unique properties that distinguish one cell type from another, e.g., density, size, unique markers, unique metabolic pathways, nutritional requirements, protein expression, protein excretion, etc. For example, cells may be selected based on density and size with the use of centrifugal gradients. Unique markers may be selected with fluorescent-activated cell sorting (FACS), immunomagnetic bead sorting, magnetic activated cell sorting (MACS), panning, etc. Unique metabolic pathways and nutritional requirements may be exploited by varying the makeup and/or quantity of nutritional ingredients of the medium on which cells are grown, particularly in a serum-free environment. Protein expression and/or excretion may be detected with various assays, e.g., ELISA.

In some embodiments, USC are selected by providing cells isolated from urine in a particular growing environment that promotes the growth of stem cells, such as stem cell medium. In some embodiments, the medium is a mixture of embryo fibroblast medium (EFM) and keratinocyte serum free medium (KSFM) (e.g., in about a 1:1 ratio, or at a ratio between 2:1 and 1:2). In some embodiments, the stem cell medium contains ¾ DMEM, ¼ Ham's F12, 10% FBS, 0.4 mg/ml hydrocortisone, $10^{-10}$ M, Citron Toxin, 5 mg/ml, insulin, 1.2 mg/ml adenine, 2.5 mg/ml transferrin plus 0.136 mg/ml 3,39,5-triiodo-L-thyronine, 10 mg/ml EGF, and 1% penicillin-streptomycin (Zhang et al., In vitro Cell Dev. Biol.-Animal 37:419, 2001).

In further embodiments, isolated USC are provided in a particular growing environment that promotes the selective differentiation of the stem cells. For example, in some embodiments USC grown in keratinocyte serum free medium develop into urothelium. In further embodiments, USC grown in DMEM with 10% fetal bovine serum develop into smooth muscle-like cells. In some embodiments, endothelial-like cells may be cultured in M199 with 20% FBS, 2 mmol/l L-glutamine, EGF (5 nl/ml) 1% sodium pyruvate and 1% penicillin-streptomycin. In some embodiments, interstitial-like cells may be cultured in DMEM with 10% FBS, 2mmol/l L-glutamine, and 1% penicillin-streptomycin.

In other embodiments, USC are selected by morphology. For example, cells isolated from urine may be diluted to a concentration allowing for the isolation of single cells (e.g., cells can be diluted to a concentration of approximately 0.5 cells/well in a multi-well plate), and observed under a microscope. Wells containing single cells can be retained for expansion, and selected by observed morphology, e.g., urothelium, smooth muscle, endothelium and/or interstitial cells.

Urine stem cells according to some embodiments of the present invention can be identified, selected, and/or isolated based on one or more "markers." Such markers include specific gene expression, antigenic molecules found on the surface of such cells, etc. In particular embodiments, urine stem cells are selected and isolated based upon the expression of at least one specific maker. In some embodiments, USC have one or more of the following markers such as CD117 (C-kit), SSEA-4, CD105, CD73, CD90, CD133, and CD44, and do not have an appreciable amount of one or more of the following markers: CD31, CD34, and CD45. Accordingly, certain embodiments embrace selecting and isolating urine stem cells which express one or more of CD117, SSEA-4, CD105, CD73, CD90, CD133, and CD44 and/or lack expression of one or more of CD31, CD34, and CD45. For example, in some embodiments a urine stem cell of the present invention is identified, selected, and/or isolated based on the expression of CD117. Urine stem cells according to some embodiments also express MSC/pericyte markers such as CD146 (MCAM), NG2 (a related antigen), and/or PDGF-Receptorβ (PDGF-Rβ). Marker expression may be probed by methods known in the art, e.g., western blot, RT-PCR, immunofluorescence, FACS, etc. In some embodiments, USC are positive for a marker selected from: CD133, SSEA-A, CD90, CD73, CD105, pericyte CD146 (MCAM), NG2, PDGF-Receptorβ (PDGF-Rβ), and combinations thereof, and wherein said cell is negative for a marker selected from CD31, CD34, CD45, and combinations thereof.

In some embodiments USC can be obtained as disclosed herein by collecting cells from a urine sample, e.g., by centrifugation, and/or directly plating the cells in or on a suitable medium, and/or selecting and isolating urine stem cells based upon stem-specific cell marker expression (e.g., via immunohistochemistry or western blot analysis). Alternatively, urine stem cells may be obtained by collecting and selecting cells via fluorescence-activated cell sorting, e.g., using a marker-specific antibody (e.g., anti-CD117 antibody) conjugated to a fluorophore (e.g., APC, phycoerythrin, allophycocyanins, fluorescein, TEXAS RED, etc.), or magnetic selection using a marker-specific antibody conjugated to magnetic particles. By way of illustration, cells may be incubated with a rabbit polyclonal antibody that specifically binds to the extracellular domain (amino acids 23-322) of the CD117 receptor protein (De Coppi, et al. (2007) Nat. Biotechnol. 25:100). The CD117-positive cells can be purified by incubation with magnetic Goat Anti-Rabbit IgG MicroBeads and selected on a Mini-MACS apparatus. Urine stem cells may also be selected with a monoclonal anti-CD117 antibody directly conjugated to MicroBeads. Any suitable method for selection including attachment to and disattachment from a solid phase is contemplated within the scope of the invention.

Urine stem cells according to some embodiments of the present invention can be routinely passaged or subcultured, e.g., by a 1:4 dilution and permitted to expand to about 50-70% confluency. Isolated populations of urine stem cells can be routinely grown and maintained under conventional culture conditions, e.g., a humidified atmosphere of 5% $CO_2$ at 37° C.

Growth may be accomplished by using initial culture in multiwell plates in a medium supplemented with 5% serum plus epidermal growth factor (EGF).

While cells of the invention can be grown in complex media with KFSM-Stem cell medium (1:1) (Zhang et al., In vitro Cell Dev. Biol.—Animal 37:419, 2001), it will generally be preferable that the cells be maintained in a simple serum-free medium such as KSFM for urothelial stem cells, or medium with 10% FBS for smooth muscle or interstitial stem cells such as Dulbecco's Minimal Essential Media (DMEM), Hank's Basic Salt Solution (HBSS), Dulbecco's phosphate-buffered saline (DPBS), RPMI, or Iscove's-modified Dulbecco's medium (TMDM), in order to effect more precise control over the differentiation of the stem cell into the desired cell.

Serum-free media used according to some embodiments includes endothelium culture medium-2 (EGM-2, Lonza). In other embodiments, a serum free media may be provided that is keratinocyte-serum free medium (KSFM, Sigma) and progenitor cell medium (PCM) in a 1:1 ratio. KSFM can be supplemented with bovine pituitary extract (50 mg/ml), and cholera toxin (30 ng/ml), but in some embodiments does not contain EGF. PCM contains DMEM and Ham's F12 basal media (3:1) supplemented with 0.4 μg/ml hydrocortisone, $10^{-10}$ M cholera toxin, 5 ng/ml insulin, $1.8 \times 10^{-4}$ M adenine, 5 μg/ml transferrin, $2 \times 10^{-9}$ M 3,39,5-triiodo-L-thyronine, and 1% penicillin-streptomycin.

Clone urine stem cell lines can also be generated by a conventional limiting dilution method either in 96-well plates or 24-well plates. Once cell colonies form, the cells are detached and transferred into multi-well dishes.

3. Differentiation of Urine Stem Cells.

Upon appropriate stimulation, USC can be differentiated into various cell types. "Differentiated" refers to cells or a population containing cells that have specialized functions, e.g., expression of known markers of differentiated cells. In this sense they are not progenitor or stem cells. For example, in some embodiments USC can differentiate into mesenchymal stem cell lineages such as osteocyte, chondrocyte, adipocyte, nerve, muscle and endothelial cells. Some embodiments of the present invention are subject to the proviso that harvested differentiated cells are not passaged under conditions to create a population of less specialized cells.

In some embodiments, USC are differentiated using methods known in the art for induction of differentiation of multipotent cells into a specific lineage, e.g., osteogenic (bone), chondrogenic (cartilage), adipogenic (fat), neurogenic (nerve), myogenic (muscle), etc. See, e.g., U.S. Patent Application publication No. 2010/0111914 to Yuanyuan Zhang et al., which is incorporated by reference herein.

In some embodiments, USC are delivered and differentiate in situ. For example, in some embodiments USC delivered to the urinary tract differentiate in situ towards skeletal muscle cells. In some embodiments, one or more growth factors are provided to promote differentiation, vascularization, innervation, etc., as desired.

In some embodiments, angiogenic growth factors are provided in the composition, e.g., a polymeric bead. In some embodiments, the polymer comprises alginate.

Angiogenic growth factors that may be provided in the polymeric bead as taught herein include, but are not limited to, VEGF (vascular endothelial growth factor) (e.g., at a concentration of from 10, 20, 30, 50, or 80 to 120, 150, 300, 500, 750, or 1000 ug/ml).

Neurogenic growth factors that may be provided in the polymeric bead as taught herein include, but are not limited to, an IGF (insulin-like growth factor) (e.g., at a concentration of 0.1, 0.25, 0.5, or 0.75 to 1,25, 1.5, 2, 3, 4, or 5 mg/ml.), nerve growth factor (NGF) (e.g., at a concentration of from 1, 2, 5, or 8 to 12, 15, 20, 25, or 30 ug/ml) and a fibroblast growth factor (FGF, e.g., FGF-1) (e.g., at a concentration of from 50, 100, 150, 200, 250, or 275 to 350, 400, 500, 750, or 1000 ug/ml).

Skeletal myogenic growth factors that may be provided in the polymeric bead as taught herein include, but are not limited to, PDGF (platelet-derived growth factor) (e.g., at a concentration of from 10, 20, 30, 50, or 80 to 120, 150, 300, 500, 750, or 1000 ug/ml) and HGF (hepatocyte growth factor) (e.g., at a concentration of from 10, 20, 30, 50, or 80 to 120, 150, 300, 500, 750, or 1000 ug/ml).

Encapsulation of growth factors can be carried out in accordance with known techniques or variations thereof that will be apparent to those skilled in the art. See, e.g., U.S. Pat. Nos. 6,783,964 and 6,365,385 to Opara, the disclosures of which are incorporated by reference herein in their entirety.

In some embodiments, heparin may be included in the beads or composition (e.g., from 1, 2, 3, or 4 to 6, 8 or 10 units per ml).

Polymeric beads useful in the present invention comprise a polymeric matrix or membrane which permits the controlled diffusion or release of biologically active molecules incorporated therein. In some embodiments, the polymeric beads comprise alginate.

The beads may be of any suitable size, such as from 10, 20 or 30 microns in diameter, up to 1000, 2000, or 5000 microns in diameter. The beads may be administered after production, refrigerated and/or cryopreserved for subsequent use, and/or loaded with bioactive molecules for subsequent use, as desired. Beads may be washed (e.g., in sterile physiological saline solution) prior to formulation and/or administration, as needed depending upon their manner of production.

Determination of whether a USC has differentiated into a specific type of cell can be achieved by morphological analysis and/or the detection of markers specific to these cell types and as generally known in the art.

Moreover, if desired, the cells can be frozen or cryopreserved prior to use, and then thawed to a viable form. Methods of freezing or cryopreserving cells (for subsequent return to viable form) are well known in the art. For example, cryopreservation of cells can involve freezing the cells in a mixture of a growth medium and another liquid that prevents water from forming ice crystals, and then storing the cells at liquid nitrogen temperatures (e.g., from about −80 to about −196° C.). See, e.g., U.S. Pat. No. 6,783,964.

Urine stem cells and/or cells differentiated from urine stem cells as disclosed herein find use in a variety of methods of treatment. "Treat" as used herein refers to any type of treatment that imparts a benefit to a patient, e.g., a patient afflicted with or at risk for developing a disease. Treating includes actions taken and actions refrained from being taken for the purpose of improving the condition of the patient (e.g., the relief of one or more symptoms), delay in the onset or progression of the disease, etc.

Diseases that may be treated with the methods disclosed herein include, but are not limited to, augmentation or replacement of urinary tract tissues. For example, urine stem cells may be used in treating diseases and conditions of the urinary tract, e.g., bladder exstrophy; bladder volume insufficiency; reconstruction of bladder following partial or total cystectomy; repair of bladders, kidneys or ureters damaged by trauma; urological cell therapy for patient with stress urinary continence and vesicoureteral reflux, and the like. Treatment in accordance with some embodiment involve urinary tract diseases and conditions such as congenital abnormalities, cancer, trauma, radiation, infection, iatrogenic injuries, nerve injury or other causes. Generally, treatment involves altering urinary tract function; improving urinary tract function; or reconstructing, repairing, augmenting, or replacing damaged urinary tract cells or whole tissues or organs to prevent or treat diseases or conditions of the urinary tract. In this regard, urine stem cells can be used in tissue engineering of urinary tract structures such as ureters, bladders, urethra, renal pelvic, kidney, bone, cartilage, muscle, skin, and the like.

Furthermore, USC find application in the pharmacology of the lower urinary tract and as a non-invasive diagnostic tool for detection of nephrological and/or urinary tract diseases. Cells according to some embodiments of the present invention can be used to diagnose diseases such as hematuria or tumors in the urinary tract system, e.g., tumors of the bladder, renal pelvic, kidney, ureters, prostate gland and urethra; renal diseases such as renal diabetes, renal tubule necrosis, acute or chronic renal failure, and renal rejection after renal transplantation; and other diseases including interstitial cystitis, neuropathic bladder, irradiated bladder, and vesicoureteral reflux or reflux nephropathy. See, e.g., U.S. Pat. Nos. 5,733,739, 5,325,169 and 5,741, 648. Examples include, but are not limited to, kidney tumor (clear cell tumor), kidney/ureter transitional cancer, non-invasive bladder cancer (Ta, T1 and CIS), invasive bladder cancer (T2 and above), non-invasive prostate cancer, invasive prostate cancer, diabetes nephropathy, cystitis caused by diabetes, interstitial cystitis, radiational cystitis, renal tubule necrosis, acute renal failure, chronic renal failure, obstruction bladder, urinary incontinence, neuropathic bladder, versicoureteral reflux/reflux nephropathy, ureteropelvic junction obstruction, acute rejection after renal transplantation, chronic rejection after renal transplantation, polycystic kidney disease, kidney stone, etc. Detection may be performed by isolating, culturing and identifying the diseased cells from the collected sample in accordance with techniques known in the art.

Urine stem cells (USC) and cells differentiated from USC find use as a cell source for cell based therapies or tissue engineering. For example, USC may be used in treatment of stress urinary incontinence, in treatment of vesicoureteral reflux, in treatment of muscle dystrophy, in treatment of renal failure, in treatment of cardiac diseases (ischemia heart disease), in treatment of esophageal reflux, in treatment of spinal injury, in treatment of mental diseases such as Parkinson's disease and Alzheimer's disease, as a potential cell source for urinary bladder tissue engineering for patients with bladder cancer and dystrophy (in some embodiments collected from the upper urinary tract to avoid collection of disease cells from the lower urinary tract), for skin substitute in treatment of skin wound or burn injury, plastic surgery in need of a cell source to repair defects, etc. USC from the upper urinary tract may be used for urethral reconstruction with tissue engineering technology.

In some embodiments, USC and/or differentiated USC may be used in the treatment of urinary incontinence. For example, USC and/or USC differentiated into a skeletal myogenic lineage may be used in treatment of urinary stress incontinence in men in which there is urethral sphinctic dysfunction. USC and/or USC differentiated into a smooth muscle cell lineage may be used in treatment of urinary stress incontinence in women in which there is pelvic floor muscle dysfunction.

In some embodiments, USC and/or differentiated USC may be used in the treatment of vesicoureteral reflux, in which there is a smooth muscle tissue defect at the ureteral orifice. In accordance with the present invention, in some embodiments treatment involves administration of an effective amount of urine stem cells, e.g., undifferentiated, differentiated or mixtures thereof, to a subject in need of treatment thereby ameliorating or alleviating at least one sign or symptom of the disease or condition of the subject.

In applications where tissues are implanted, in some embodiments cells are of the same species as the subject into which the tissue is to be implanted. In some embodiments cells are autogeneic (i.e., from the subject to be treated), isogeneic (i.e., a genetically identical but different subject, e.g., from an identical twin), allogeneic (i.e., from a nongenetically identical member of the same species) or xenogeneic (i.e., from a member of a different species).

In some embodiments, when cells of the invention are used for treating a subject, the cells are formulated into a pharmaceutical composition containing the cells in admixture with a pharmaceutically acceptable vehicle or carrier (e.g., a collagen gel). Such formulations can be prepared using techniques well known in the art. See, e.g., U.S. Patent Application 2003/0180289; Remington: *The Science and Practice of Pharmacy*, Alfonso R. Gennaro, editor, 20th ed. Lippincott Williams & Wilkins: Philadelphia, Pa., 2000 . In the manufacture of a pharmaceutical formulation according to the invention, the cells are typically admixed with, inter alia, an acceptable carrier. The carrier must, of course, be acceptable in the sense of being compatible with any other ingredients in the formulation and must not be deleterious to the patient. The carrier may be a solid or a liquid, or both (e.g., hydrogels), and can be formulated with the cells as a unit-dose formulation. In one embodiment the cells are provided as a suspension in the carrier to reduce clumping of the cells.

In some embodiments a temperative sensitive gel may be used. Examples of temperature sensitive gels include thermaosensitive hydrogels and thermosensitive polymer gels (e.g., a poloxamer such as Pluronic® F-127 (BASF corporation, Mont Olive, N.J.)). See also U.S. Pat. Nos. 6,201,065, 6,482,435.

In some embodiments, cells are administered in conjunction with other types of cells. For example, in some embodiments USC are administered in conjunction with endothelial cells such as human umbilical vein endothelial cells (HUCEC) in order to promote vascularization. In some embodiments, USC are administered in conjunction with compounds such as one or more growth factors as taught herein. The administration of two or types of cells and/or compounds, etc. "in combination" or "in conjunction" means that the two types of cells and/or compounds are administered closely enough in time to have an additive and/or synergistic effect. They may be administered simultaneously (concurrently) or sequentially. Simultaneous administration may be carried out by mixing prior to administration, or by administering them at the same point in time but at different anatomic sites or using different routes of administration.

In another embodiment, the cells are formulated in an encapsulated form (e.g., encapsulated in a capsule that is permeable to nutrients and oxygen to sustain the viability of the cells in vivo). Materials and methods for the encapsulation of cells in permeable capsules are well known and described in, for example, U.S. Pat. No. 6,783,964 . For example, the cells may be encapsulated in a microcapsule of from 50 or 100 µm to 1 or 2 mm in diameter that comprises an internal cell-containing core of polysaccharide gum surrounded by a semipermeable membrane; a microcapsule that comprises alginate in combination with polylysine, polyornithine, and combinations thereof. Other suitable encapsulating materials include, but are not limited to, those described in U.S. Pat. No. 5,702,444.

In further embodiments, formulations of the invention include those for parenteral administration (e.g., subcutaneous, intramuscular, intradermal, intravenous, intraarterial, intraperitoneal injection) or implantation. In some embodiments, administration is carried out intravascularly, either by simple injection, or by injection through a catheter positioned in a suitable blood vessel, such as a renal artery. In another embodiment, administration is carried out as a graft to an organ or tissue to be augmented, as discussed above.

In some embodiments, cells are administered to the urethra. For example, cells may be administered at the site of one or more of the sphincter muscles of the urethra. The sphincter muscle unit of the urethra has both internal and external sphincter muscles. The internal sphincter is the extension of the detrusor muscle (the primary muscle for forcing urine out of the bladder), is made of smooth muscle under involuntary or autonomic control. By contrast, the external sphincter is made of skeletal muscle under voluntary control of the somatic nervous system. Other connective tissues around the urethra, including vessels and peripheral nerves, also play important roles in control of micturition. Urinary incontinence may result from muscle weakness or injuries, nerve damage, or vascular (blood supply) changes, all of which may be alleviated in some embodiments of the present stem cell therapies. Unlike using bulking materials to mechanically squeeze the urethra, a longer-term strategy to treat SUI is to repair defects of both skeletal and smooth muscle, and to improve the blood supply and innervation in the mid-urethral segment. In some embodiments, cells are administered (e.g., by injection) into the middle urethra.

Formulations of the present invention suitable for parenteral administration include sterile liquid, preferably aqueous, injection compositions of the cells, which preparations may be isotonic with the blood of the intended recipient. These preparations can also contain anti-oxidants, buffers, bacteriostats and solutes that render the formulation isotonic with the blood of the intended recipient. The preparations are, apart from the cells being administered, sterile in the sense that they are free of microbial contaminants such as bacteria and viruses. The formulations can be in a synringeable, injectable form, can be in a form suitable for surgical implantation, or in any other form suitable for administration into the subject.

According to some embodiments, the cells administered to the subject can be syngeneic (i.e., isologous, including isogeneic and autogeneic), allogeneic (i.e., homologous) or xenogeneic (i.e., heterologous) with respect to the subject being treated, depending upon other steps such as the presence or absence of encapsulation or the administration of immune suppression therapy of the cells.

The therapeutically effective dosage of cells will vary somewhat from subject to subject, and will depend upon factors such as the age, weight, and condition of the subject and the route of delivery. Such dosages can be determined in accordance with procedures known to those skilled in the art. In general, in some embodiments, a dosage of $1\times10^5$, $1\times10^6$ or $5\times10^6$ up to $1\times10^7$, $1\times10^8$ or $1\times10^9$ cells or more per subject may be given, administered together at a single time or given as several subdivided administrations. In other embodiments a dosage of between $1$-$100\times10^8$ cells per kilogram subject body weight can be given, administered together at a single time or given as several subdivided administrations. Of course, follow-up administrations may be given if necessary.

For allogenic transplant into a patient, cells and/or tissues as described herein may be matched or tissue-typed in accordance with known techniques, and/or the subject may be administered immune suppressive agents to combat tissue transplant rejection, also in accordance with known techniques. If desired or necessary, the subject can also be administered an agent for inhibiting transplant rejection of the administered cells, such as rapamycin, azathioprine, corticosteroids, cyclosporin and/or FK506, in accordance with known techniques. See, e.g., U.S. Pat. Nos. 5,461,058; 5,403,833; and 5,100,899; see also U.S. Pat. Nos. 6,455,518; 6,346,243; and 5,321,043.

Moreover, cells of the present invention can be transfected (e.g., with a specific gene) prior to seeding with genetic material. Useful genetic material may be, for example, genetic sequences that are capable of reducing or eliminating an immune response in the host. For example, the expression of cell surface antigens such as class I and class II histocompatibility antigens can be suppressed. This would allow the transplanted cells to have a reduced chance of rejection by the host.

The present invention is explained in greater detail in the following non-limiting examples.

EXAMPLES

To provide site-specific delivery and targeted release of growth factors to implanted urine-derived stem cells (USCs), we fabricated biodegradable polymer microspheres of alginate containing growth factors. The growth factors included VEGF, IGF-1, FGF-1, PDGF, HGF and NGF. Release from the microbeads in vitro was assessed by a gamma counter over 4 weeks. Biologically active VEGF was released, as assessed by endothelial differentiation of USCs in vitro. Twenty-eight days later, USC-microbeads embedded in type I collagen gel (2 mg/ml) were injected subcutaneously into nude mice. It was found that grafted cell survival was improved and more cells expressed myogenic and endothelial cell transcripts and markers compared to controls. More vessel formation and innervations were observed in USCs combined with six growth factors contained in microbeads compared to controls. In conclusion, a combination of growth factors induced USCs to differentiate into a myogenic lineage, enhanced revascularization and innervation, and stimulated resident cell growth in vivo. This approach could potentially be used for cell therapy in the treatment of stress urinary incontinence.

Stress urinary incontinence (SUI) is most common in people older than 50 years of age; these are primarily women, but there is an increasing number of male patients as well [1, 2]. Urinary incontinence affects up to 13 million people in the United States and 200 million worldwide. The cost of treating urinary incontinence in United States alone is $16.3 billion annually [3].

SUI is associated with the loss of various amounts of urine when intra-abdominal pressure increases because of dysfunction of the urethral sphincter or the pelvic floor muscles. Besides pharmacotherapy [4], several invasive surgical therapies, including sling surgical procedures [5] and injection of bulking agents [6], have been commonly used to treat SUI. Sub-urethral slings, such as the transvaginal or transobturator tape procedures, have success rates of around 70% [5]. Although the sling procedure can enforce the weakness of pelvic floor muscles, the urethral sphincter deficiency remains [7].

Bulking procedures are particularly useful for treating SUI in patients who wish to avoid open surgical procedures [6]. A variety of biomaterials, such as bovine collagen [8], calcium hydroxyapatite, silicone [9], carbon beads [10] polydimethylsiloxane (Macroplastique), and polytetrafluoroethylene (PTFE; Teflon) [11], have been used to insert bulk around the urethra and thereby raise its outlet resistance. This provides closure of the sphincter without obstructing it, and is most effective in patients with a relatively fixed urethra. Although injection of bulking agents has provided encouraging outcomes, over time these agents are absorbed and can cause chronic inflammation, periurethral abscess, foreign body giant cell responses, erosion of the urinary bladder or the urethra, migration to inner organs, obstruction of the lower urinary tract with resultant urinary retention, severe voiding dysfunction, and even pulmonary embolism [6, 12-14].

Cell-based therapy is an alternative to restore deficient urethral sphincter function in the treatment of SUI. Several investigations have focused on autologous stem cells derived from skeletal muscle or fat tissues [15, 16], with success rates ranging from 12 to 79% [17]. To obtain these stem cells, invasive procedures such as bone marrow or fat aspiration are usually involved, with an attendant risk of complications. We recently demonstrated that stem cells exist in human voided urine or urine drained from upper urinary tract. These cells, termed urine stem cells (USCs), possess stem cell characteristics with robust proliferative potential and multi-potential differentiation [18-22]. These cells can be obtained using simple, safe, non-invasive and low-cost procedures, thus avoiding the adverse events associated with obtaining cells from other sources. Our recent studies demonstrated that adding exogenous angiogenic factors, such as transfection of the VEGF gene, significantly promoted myogenic differentiation of USCs and induced angiogenesis and innervation [21]. However, VEGF delivered by virus caused several side effects in our animal model, including hyperemia, hemorrhage, and even death [23]. Thus, it is desirable to employ a safer approach in stem cell therapy to increase angiogenesis and promote muscle regeneration.

Biodegradable polymers, specifically biocompatible hydrogels that deliver molecules in a controlled fashion, can be beneficial as delivery vehicles to promote regeneration and tissue healing [24]. Alginate is one of the most commonly used natural hydrogels as an aqueous drug carrier for encapsulation because of its biocompatibility. Because alginate is a hydrophilic and negatively charged polymer, alginate microspheres also resist protein adsorption and thus do not cause an immune response [25]. Alginate microsphere beads can stably release active FGF-1 for at least 3 weeks in vitro, and this sustained release of FGF-1 promoted neovascularization in vivo without any side effects[26-28].

Our more recent data showed that USCs display myogenic and endothelial differentiation capacity when cultured in media containing the associated growth factors [29, 30]. Our hypothesis was that skeletal myogenic, angiogenic, and neurogenic growth factors released from alginate microsphere beads can induce USCs to give rise to a skeletal myogenic lineage, improve revascularization and innervations, and recruit resident cells to take part in tissue repair. Therefore, in the present study, we examined whether a synergistic mixture of growth factors could be released efficiently and in a controlled manner from alginate microsphere beads, thus guiding USCs to cell differentiation and enhancing tissue regeneration for potential use in cell therapy of SUI.

2. Materials and Methods 2.1 Fabrication of alginate microsphere beads. A low-viscosity (<20 m Pas) ultrapure alginate with high guluronic acid (LVG) content (60% guluronate monomer units) was used for this study (Nova Matrix, Sandvika, Norway). LVG (1.5 wt %) was prepared in minimum essential medium (MEM) with calcium-free serum and stored at 4° C. The LVG microcapsules were generated using an eight nozzle flow-focusing device at the flow rate of 1.4 ml/min and air pressure at 1.5 psi. These capsules were collected in a calcium chloride solution (1.1 w/t %) and cross-linked for 15 min. Finally, these capsules were washed three times with Hank's buffered salt solution (HBSS) with calcium. The amounts of growth factors embedded in alginate beads were determined according to the effective dose (ED 50) provided by the manufacturer. A solution of 100 µg/ml PDGF-BB (4 µg) and 100 ug/ml HGF (10 µg) served as a skeletal myogenic promoter; 100 ug/ml VEGF (7 µg) as the angiogenesis inducer; and a combination of 1 mg/ml IGF (14 µg), 10 ug/ml NGF (0.5 µg), 300 ug/ml FGF-1 (1 ug) to promote innervation. Five Units/ml heparin was added in the microsphere beads. Each growth factor mixture was decreased to one-third of the original amount when these three parts were combined, to document synergistic effects (Table 1).

2.2 Measurement of growth factor release. The growth factor release efficiency was evaluated in vitro when single, bi- or multi-combined growth factors were loaded within alginate microsphere beads. To preload the microbeads with growth factors, about 0.5 g of capsules was incubated overnight with 0.5 ml of I-125 labeled growth factor solutions (VEGF and IGF, Phoenix Pharmaceuticals, Inc.) and unlabeled NGF and FGF-1 (Protech) in an Eppendorf tube on a shaker at 4° C. The supernatant was removed and the capsules were washed three times with HBSS (with $Ca^{2+}$) to remove unincorporated growth factors. To measure the release kinetics of I-125-labeled growth factors embedded in alginate microcapsules, the capsules were suspended in 0.5 ml of HBSS and incubated at 37° C. The supernatant was replaced fully at pre-determined time points (FIG. 1) and read in a gamma counter (Model 2470, PerkinElmer). Counts per minute (CPM) were measured and corrected for radioactivity decay.

2.3 Cell culture. Fresh human urine, umbilical cord, and human skeletal muscle specimens collected in orthopedic surgery were used for this study according to a protocol approved by the Wake Forest University Health Sciences Institutional Review Board. Fifteen voided urine samples (100-400 ml) from two healthy men (25 and 40 years old, respectively) were collected and immediately transferred to the laboratory for isolation and culture, as reported previously [22]. Briefly, urine specimens were centrifuged at 500×g for 5 min and the supernatant was removed. The cell pellet was gently re-suspended in mixed media composed of embryo fibroblast medium (EFM) and keratinocyte serum free medium (KSFM) (1:1 ratio) and plated in 24-well plates (p0). Individual clones appeared 3-5 days after plating. Each single cell clone was trypsinized and transferred into 6-well dishes when the cells reached a confluence of 70-80% (p1). Finally, cell cultures were transferred to a 150 mm culture dish (p2) for expansion; USCs at p3-4 were used for most experiments.

Human umbilical cord endothelial cells (HUVECs) were isolated by brief perfusion of enzyme (specify the enzyme) solution into umbilical cord veins [31]. HUVECs were then cultured on plates coated with fibronectin (Millipore, Billerica, Mass.) using Endothelial Growth Medium-2 (EGM2) (Lanza Biologics, Portsmouth, N.H.) containing 2% fetal bovine serum (FBS) at 37° C. in a 5% $CO_2$ cell incubator. Cultured HUVECs were used as positive control in the assessment of angiogenesis.

Human skeletal muscle cells were isolated from chopped muscle tissue (1 mm×1 mm) by incubation in 10 ml of collagenase-II (0.1% w/v)-dispase (4 mg/ml) solution prepared in DMEM for 1 hour at 37° C. with constant shaking (60 rpm). The liberated cells were collected (400×g) and washed with DMEM medium containing 10% horse serum and plated into a 6-well tissue culture dish. After 2 hours, the supernatant from the dish was transferred to another well and the process repeated. After 5 days in culture, the media was changed to SkGM2 (Lonza, Biologics, Portsmouth, N.H.) containing 10% FBS at 37° C. in a 5% $CO_2$ cell incubator. Cultured human skeletal muscle cells were used as control.

Endothelial differentiation of USCs. To assay the effects of growth factor releases on angiogenic differentiation of SCs, cells were cultured with alginate microsphere beads loaded with VEGF. USCs at passage 3 were seeded in a 24-well plate (1,000 cells/$cm^2$) and microsphere beads containing VEGF were added to the cell inserts (Millipore, Billerica, Mass.) on the top of wells. EGM-2 excludes VEGF from the kit, but microsphere beads containing VEGF were used for endothelial induction. EGM-2 containing 10 ng/ml VEGF was used as a positive control, and Dulbecco's modified Eagle's medium (DMEM) containing 10% FBS and 1% antibiotics penicillin and streptomycin (P/S) only or combined with VEGF beads was used as a negative control. Media were changed every three days. mRNA was collected for real-time PCR analysis of endothelial markers (CD31 and vWF) at 14 days, as previously reported[32].

In vivo implantation. A total of 24 male athymic mice at 6 weeks old (Harlan Laboratories, Indianapolis, Ind.) were used; ten groups were designated, as listed in Table 1, Cell-free or/and cytokine-free preparations were used in Groups 1-5 (controls). USCs added with six growth factors were divided into five groups: myogenic (PDGF-BB plus HGF), anigogenic (VEGF), neurogenic (IGF, NGF, and FGF-1), synergistic 1 (all six growth factors) and synergistic 2 (all growth factors plus endothelial cells). When all six growth factors were delivered together in (Groups 9 and 10), the growth factor doses in each group were reduced to one-third of those used in Groups 6-8 . USCs at p3, HUVECs, and human skeletal muscle cells (as controls) at p5 were used for cell injection.

A total of $5 \times 10^6$ cells—human skeletal muscle cells or USCs alone, or USCs plus ECs (4:1)—were embedded in 0.5 ml collagen-I gel (2 mg/ml) combined with various alginate beads according to group assignment. The cell-bead-collagen gel preparations were injected subcutaneously into 4 sites (right and left flanks in front and rear areas) per animal. All experiments were approved by the Wake Forest University Health Sciences Institutional Animal Care and Use Committee.

Macro- and Microhistologic Analysis

Graft appearance was grossly assessed at 28 days, at which paint the mice were sacrificed. After harvesting, each graft was photographed and weighed. Half of the implanted tissue specimens were frozen immediately in liquid nitrogen for real-time PCR measurements. The remaining samples were embedded in optimal cutting temperature (O.C.T.) for immunofluorescence or fixed in 10% neutral buffered formalin, dehydrated, and embedded in paraffin for histology. A 5-μm section was cut and mounted using anti-fade mounting media (Vector Laboratories). For visualization of cell density, 4',6-diamidino-2-phenylindole (DAPI) staining was performed. For histologic evaluation, routine hematoxylin and eosin (H&E) and Masson's trichrome staining was done.

To monitor the fate and differentiation of human USCs in vivo, we conducted immunofluorescent triple staining using DAPI and human nuclei antibodies combined with endothelial-, muscle-, and nerve fiber-specific markers (Table 2). Slides were visualized under a fluorescent microscope (Leica-DM 4000B, Germany) and the images recorded for analysis. For semi-quantitative analyses of new nerve fibers, sections stained with specific immunofluorescent markers and Masson's trichrome were evaluated by two independent and blinded observers using images captured by the microscope. The average total number of targeted cells was counted by semi-quantitative assessment in 10 fields under 200× magnification.

Real-time PCR. mRNA was extracted from two sources 1). Endothelial cell-USCs induced in vitro with VEGF released from microsphere beads in endothelial differentiation medium; and 2) implanted grafts. These gene samples were assessed using an RNA isolation kit (5 PRIME, Gaithersburg, Md.) according to the manufacturer's instructions. Five μg RNA was converted to cDNA in a reaction containing random primers, nucleotides, and reverse transcriptase enzyme using a high-capacity cDNA reverse transcription kit (Applied Biosystems, Foster City, Calif.). One-tenth of the cDNA was then used for real-time analysis along with Taqman Universal PCR master mix and Taqman gene expression probes according to the manufacturer's instructions, using a 7300 Real Time PCR system (Applied Biosystems, Foster City, Calif.). Reagents used for real-time RT PCR analysis were purchased from ABI (Applied Biosystems, Foster City, Calif.). The primer pairs used in this study are listed in Table 3.

Statistical analyses. Results were analyzed using one-way ANOVA (SPSS 16.0). Values are expressed as mean±standard deviation (SD). Comparisons of weight, human nuclei/DAPI ratio, real-time PCR analysis, and innervation among groups were performed by using one-way ANOVA, followed by a Student-Newman-Keuls post hoc test for multiple comparisons when appropriate. P values≤0.05 were considered as statistically significant.

3 . Results 3.1 Release of I-125-labeled growth factors. Alginate beads appeared stable and uniformly spherical after their fabrication. No broken or damaged capsules were detected. The imbedded growth factors, including I-125-labeled VEGF, IGF and unlabeled FGF-1, NGF, were released quickly in the first few days of incubation followed by a steady rate of release for a month. As expected, the release rate of IGF-1 (mw ~17 KD) was higher when present in the microbeads alone than its release rate when combined with VEGF (mw ~45 KD) in the microbeads (FIG. 1). In contrast the release of VEGF when present alone in the microbeads was not different from its release in when combined with other growth factors in the microbeads (FIG. 1). The same steady state of slow release trend was constant over 30 days, regardless of combination strategies. After the in vitro release was complete, no remaining growth factors were detected, indicating all the cytokines were successfully released from the microcapsules.

Figure 2A:
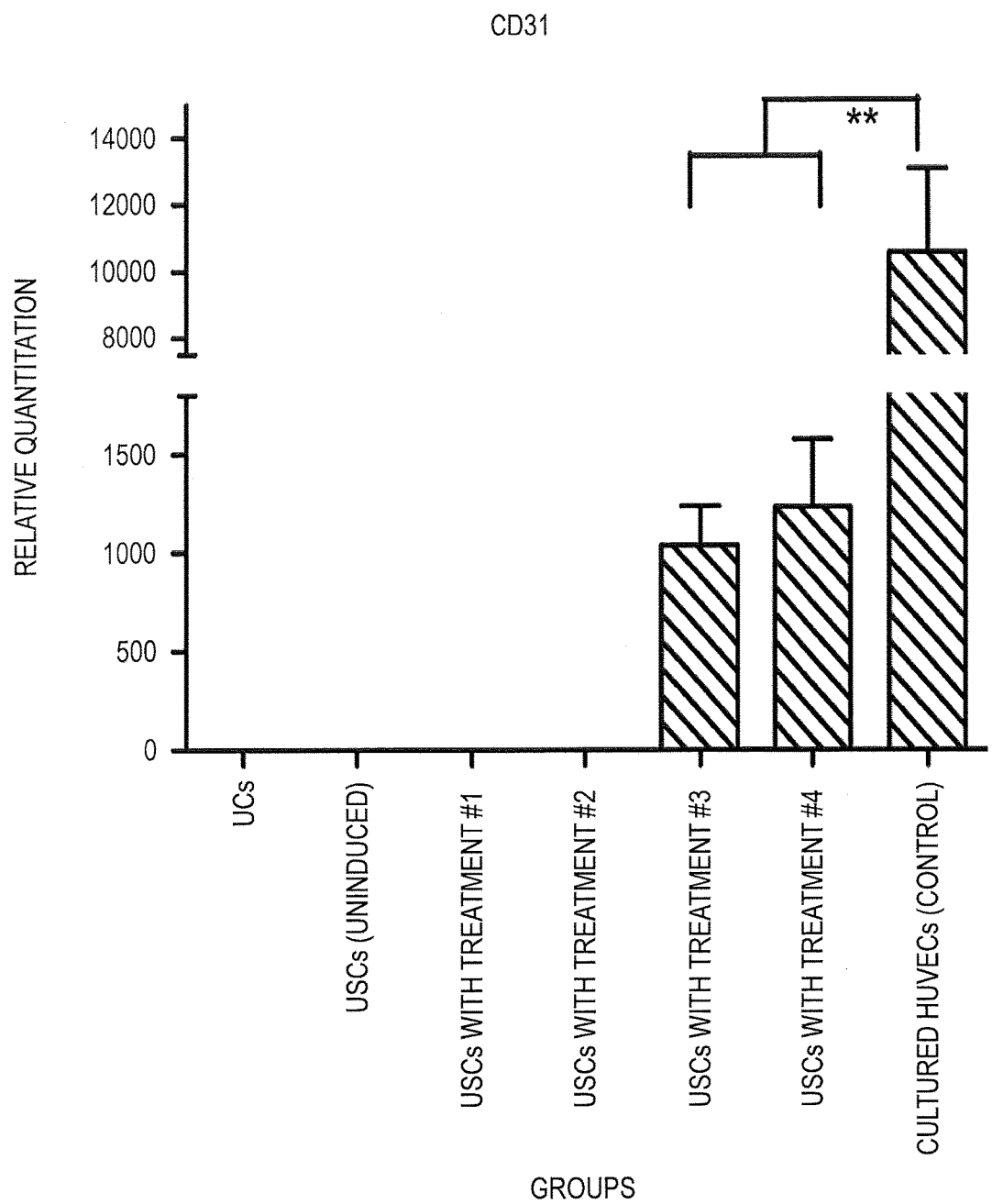
FIGS. 2A-2B. Endothelial gene expression of USCs in vitro. USC (P3) were seeded at 1,000 cells/cm$^2$ and induced by endothelial differentiation media as follows: Treatment$^{\#}$1=DMEM (10% FBS) with VEGF alginate beads located in transwell; Treatment$^{\#}$2=DMEM (10% FBS+1% P/S); Treatment$^{\#}$3=EC induced medium (EGM-2) plus alginate microsphere beads loaded with VEGF; Treatment$^{\#}$4=Endothelial cell-induced medium including VEGF solution (10 ng/ml). Significant increase of endothelial cell-specific gene expression CD31 (FIG. 2A) and vWF (FIG. 2B) could be detected in both Treatments #3 and 4, regardless of whether VEGF was added directly to the medium or delivered by the alginate beads. Urothelial cells (UC) were the negative control and human umbilical vein endothelial cells (HUVEC) were the positive control.
Figure 2B:
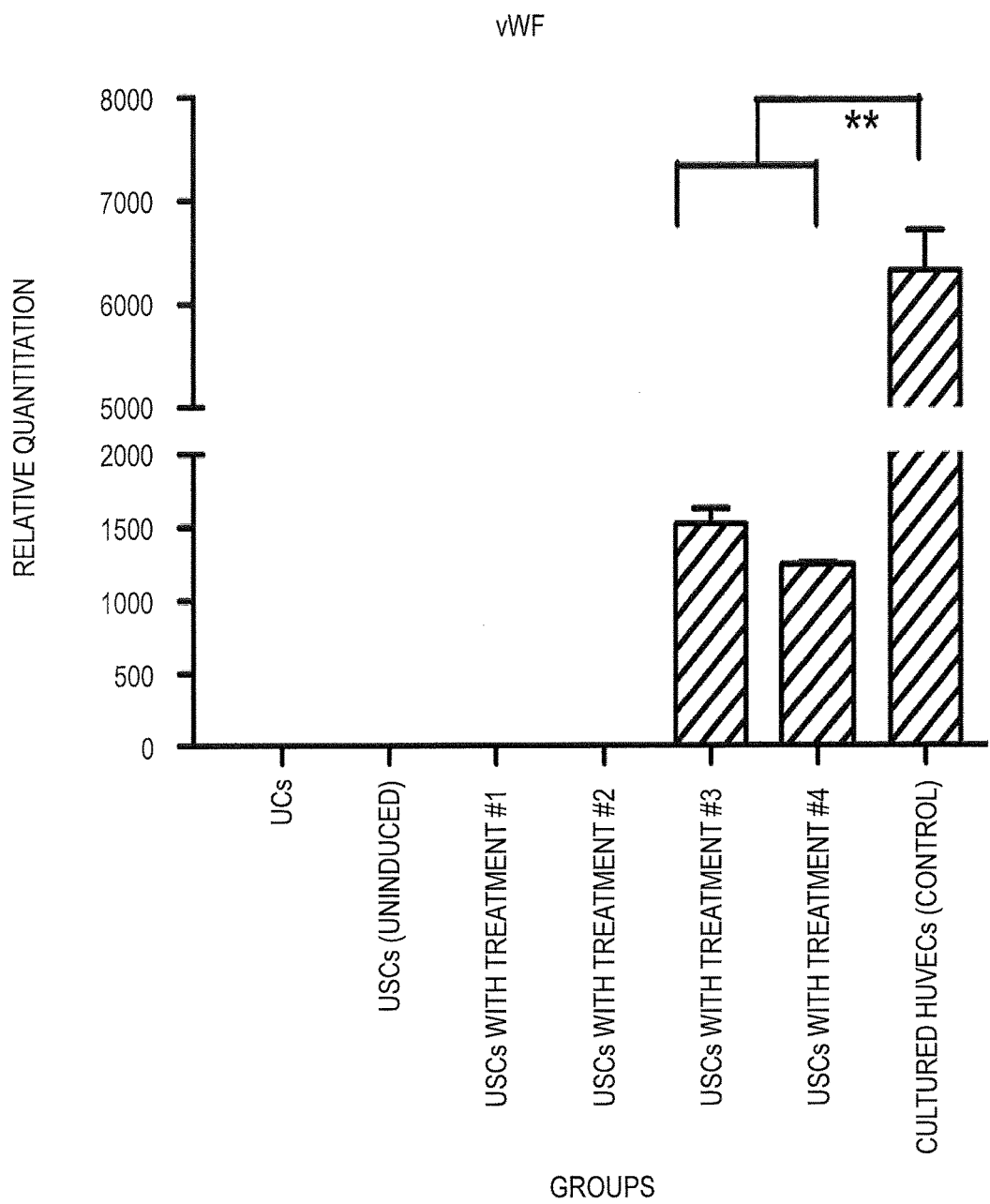

3.2 Endothelial differentiation of USCs in vitro. After USCs were cultured in the induced medium with VEGF-loaded beads for 14 days, gene expression of endothelial markers (CD31 and vWF) was significantly increased compared to negative controls (non-induced USCs and urothelial cells) (p<0.05) (FIGS. 2A-2B). Moreover, endothelial gene expression of USCs induced in the medium with VEGF-beads was similar to expression in USCs treated with medium with VEGF, indicating that VEGF was efficiently releasing from the microspheres.

Figure 3A:
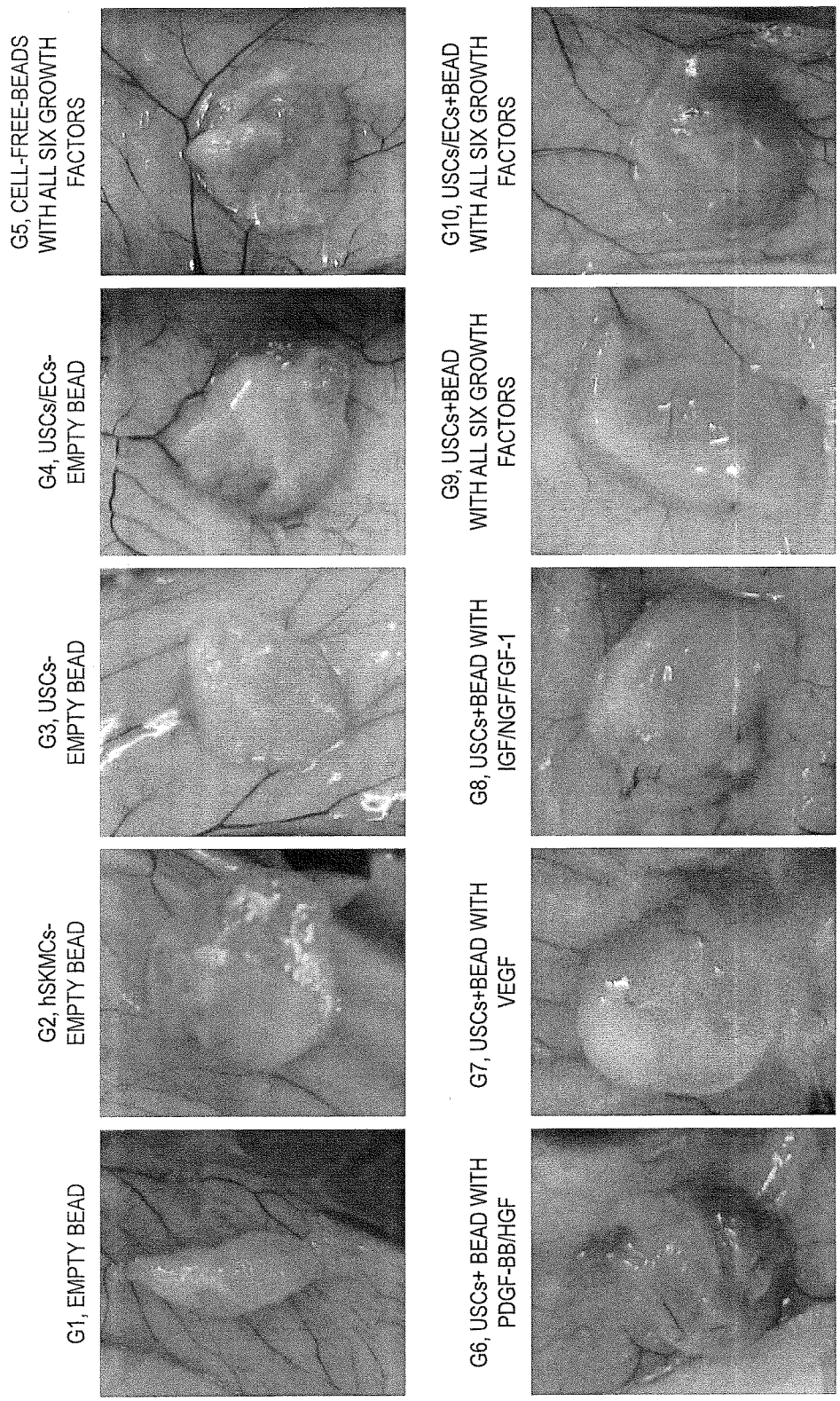
FIGS. 3A-3E. Gross appearance, graft weight, histochemical staining, and immunostaining of the implanted grafts after 4 weeks in vivo.
Figure 3B:
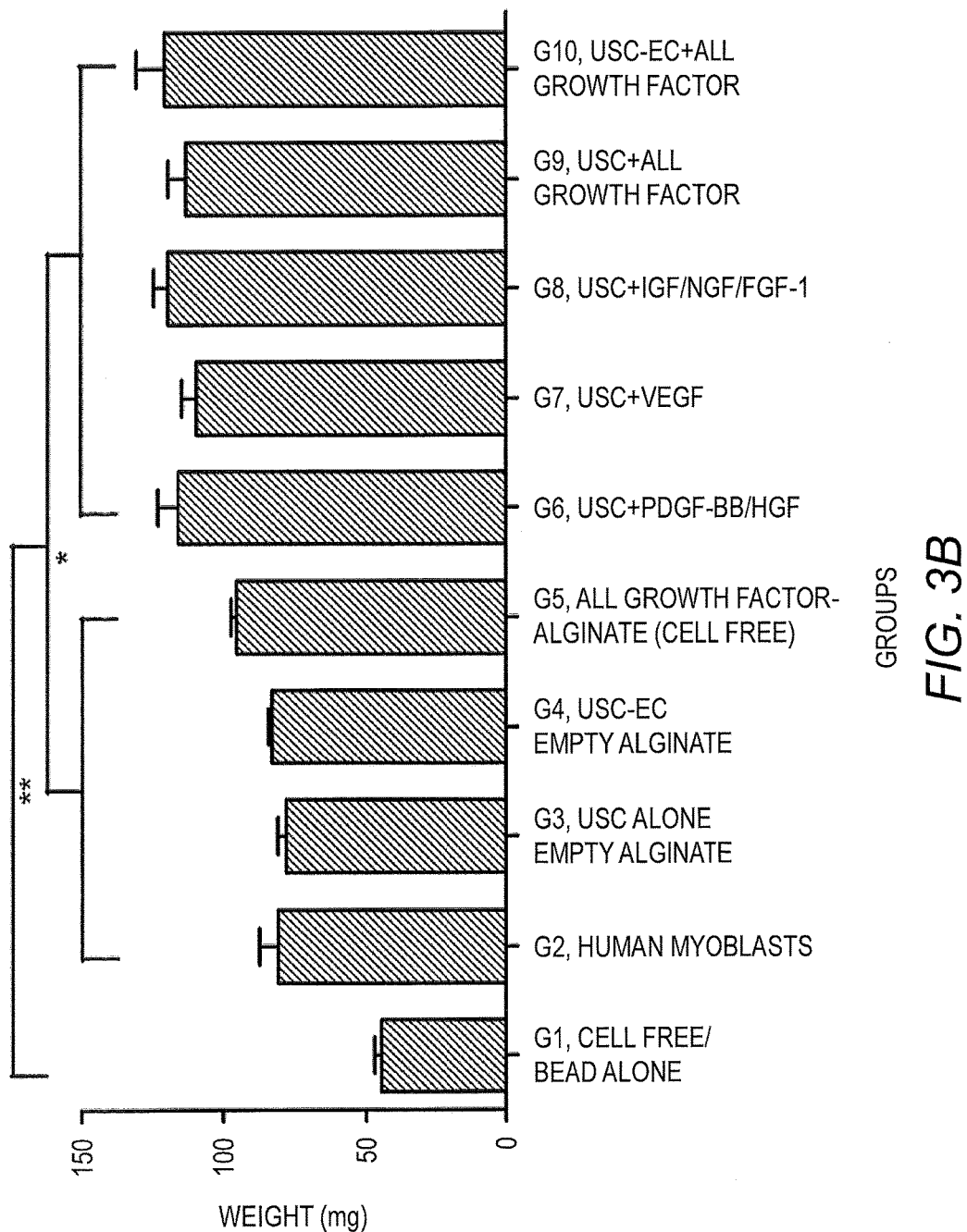

3.3 Gross assessment of implanted grafts. More capillary formation was observed in the USCs combined with various growth factors embedded in beads (Groups 6-10), compared to the other groups (FIG. 3A). Although implant sizes were similar among 9 of the 10 groups (grafts were smaller in Group 1), the weight of implanted grafts in USCs combined with the microspheres containing growth factors (Groups 6-10) significantly increased compared to those in Groups 2-5 (p<0.05) (FIG. 3B). No significant differences in weight were seen among Groups 6-10 . This was also true among the control groups (Groups 2-5). Importantly, no tumors were found and no animals died during the 28 days of subcutaneous implantation.

Figure 3C:
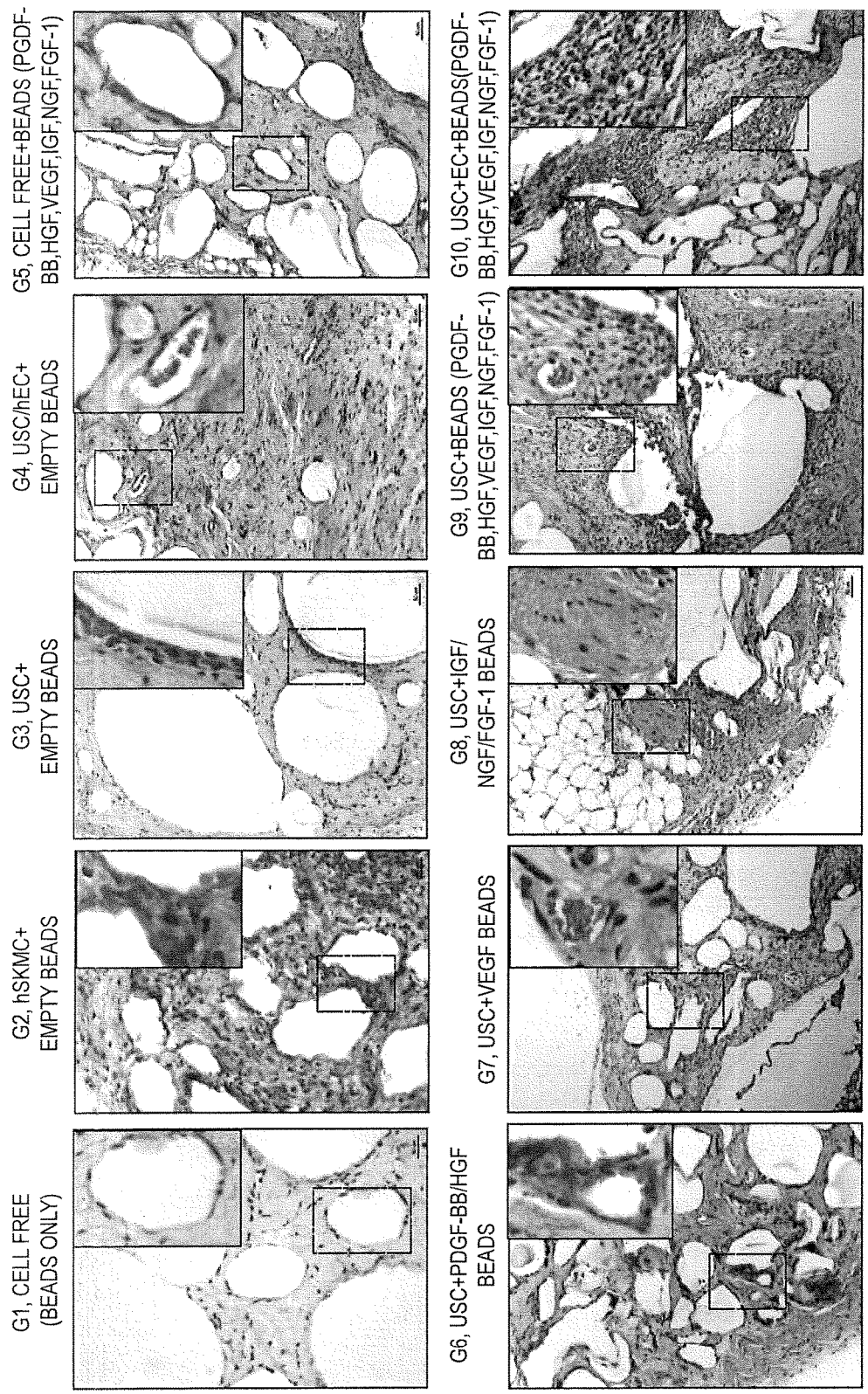
Figure 3D:
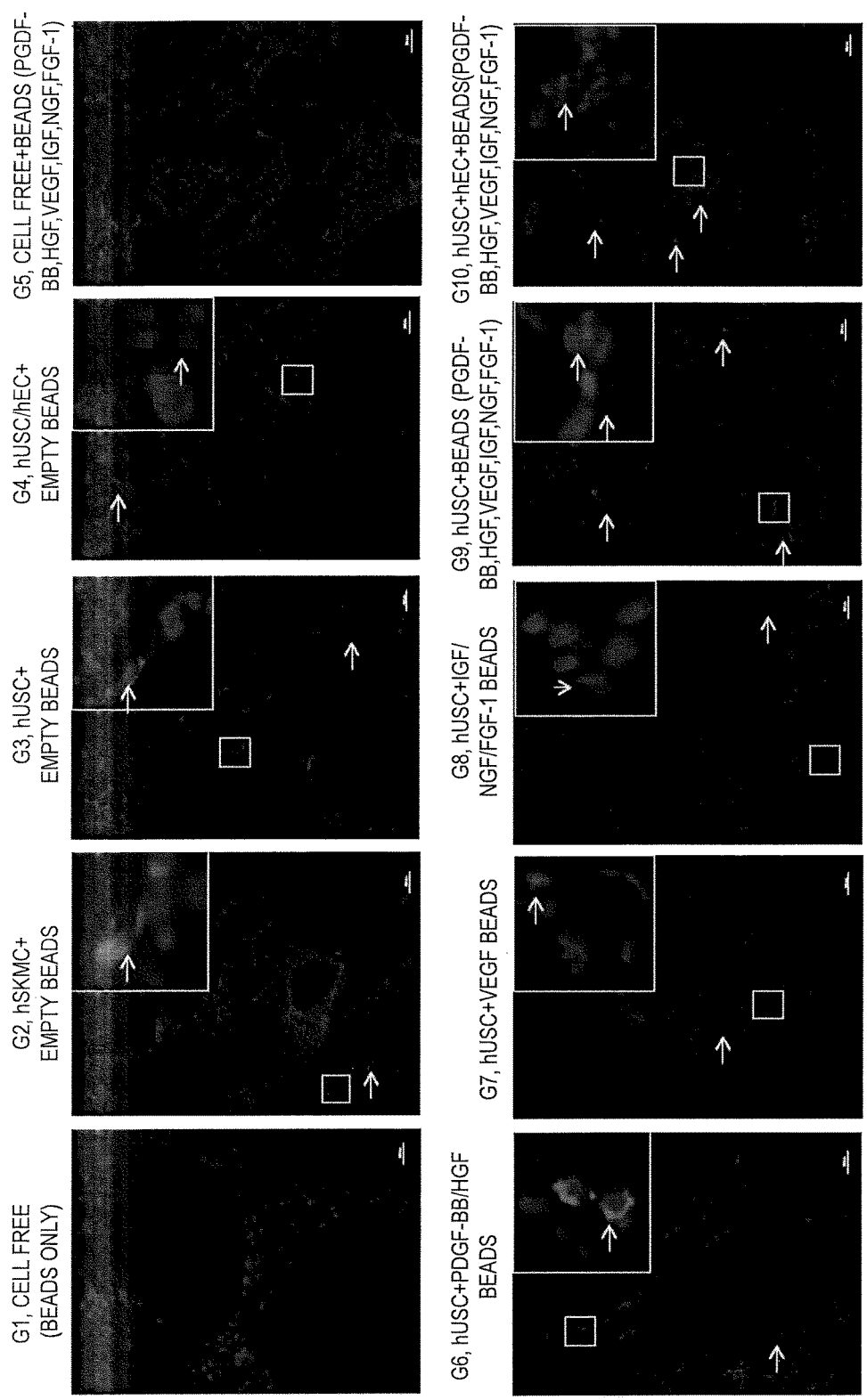
Figure 3E:
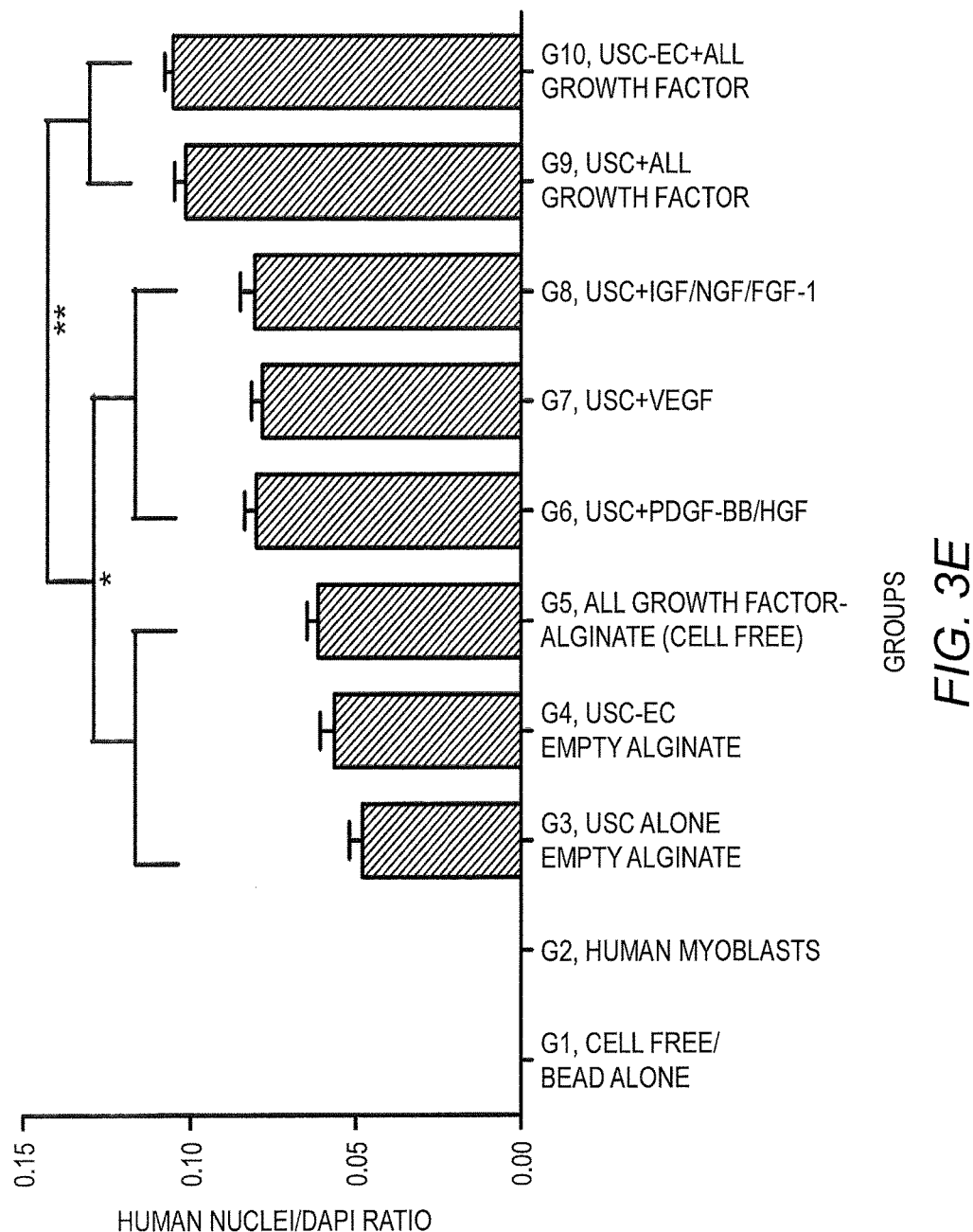

3.4 Real-time PCR analysis, histology, and immunocytochemistry. More implanted cells with human nuclei protein expression and resident cells were found surrounding the beads in Groups 6-10, especially in Groups 9-10, based on the high ratio of human nuclei/DAPI staining, compared to the other groups after 28 days after subcutaneous implantation (FIGS. 3C-E).

Figure 4A:
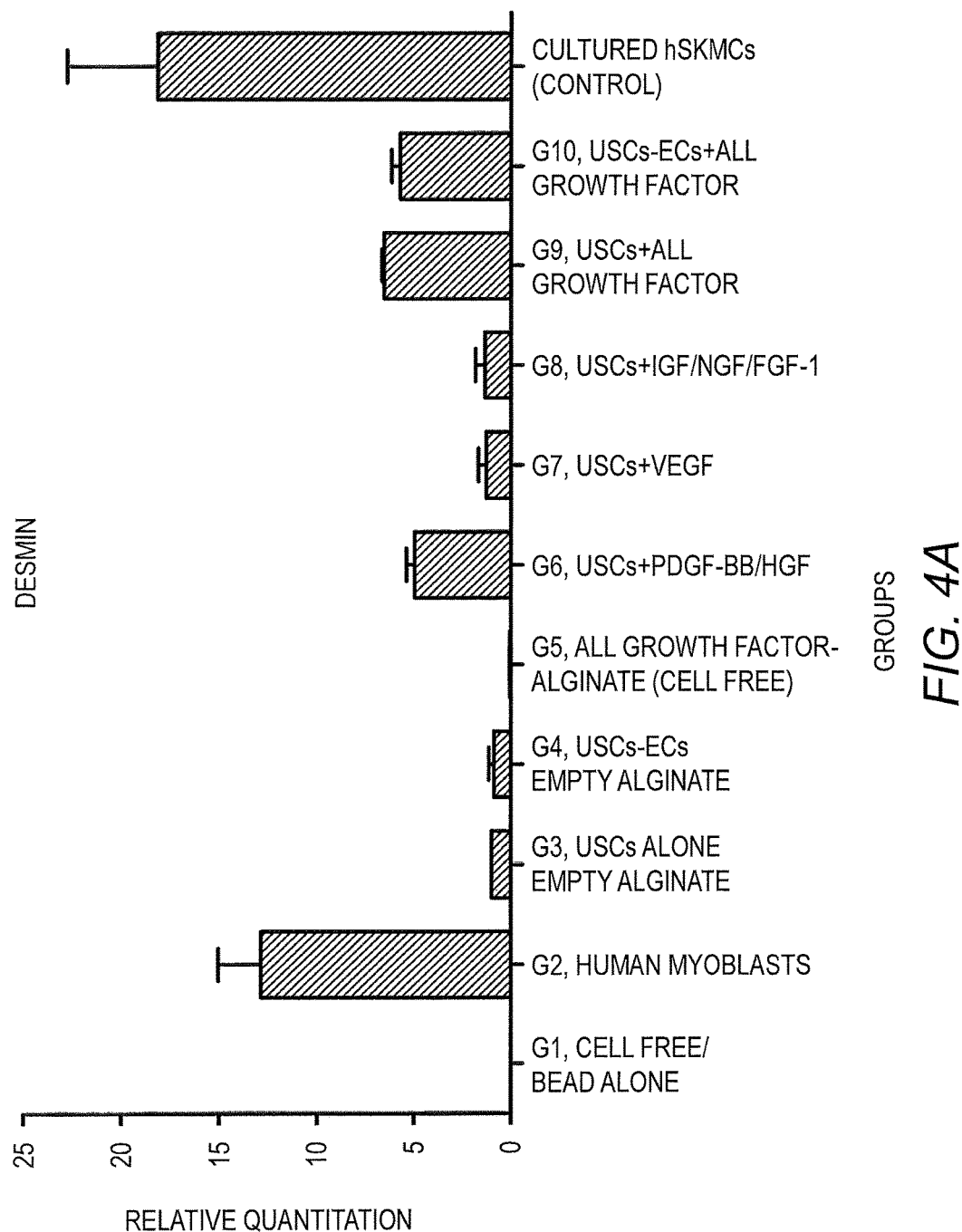
FIGS. 4A-4F. Expression of skeletal myogenic-specific marker on induced USCs in vivo assessed with quantitative PCR and immunofluorescent staining. Quantitative real-time PCR performed on total RNA for all groups using human myogenic-specific primers (desmin (FIG. 4A), MyoD (FIG. 4B), and Myf-5 (FIG. 4C)). Implants of different treatment groups of USC (p3) were harvested after 4 weeks in vivo. Groups 1, and 2 had hSKMC injection. Groups 3, 5, 6, and 9 were subjected to immunofluorescent staining using skeletal myogenic markers (desmin (FIG. 4D), MyoD (FIG. 4E), and Myf-5 (FIG. 4F)) and human nuclei specific marker. Specific areas of staining (depicted by white arrows) appear green (desmin, MyoD, and Myf-5) and red (Human nuclei) Nuclei were counterstained with DAPI (blue). Scale bar=50 µm.
Figure 4B:
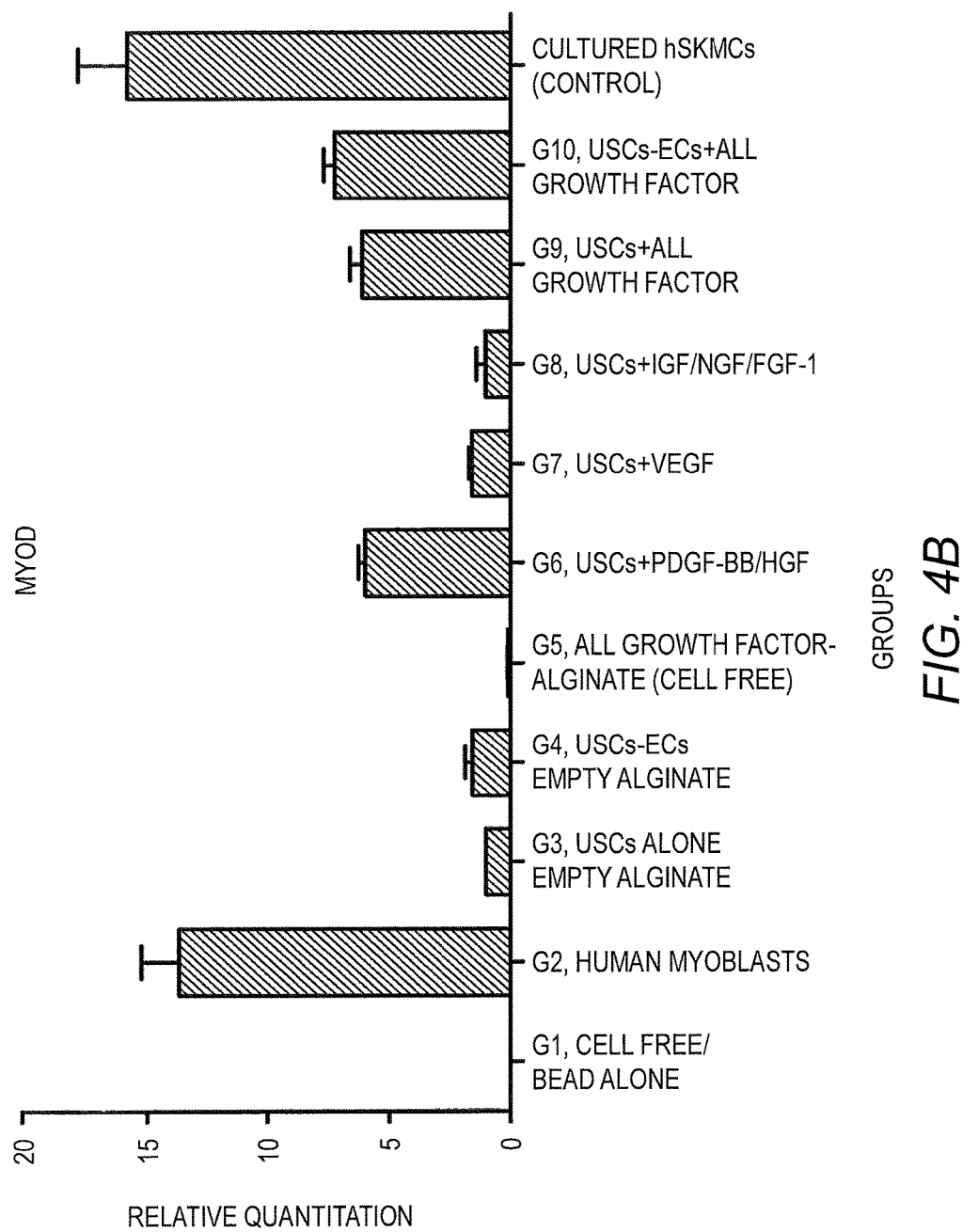
Figure 4C:
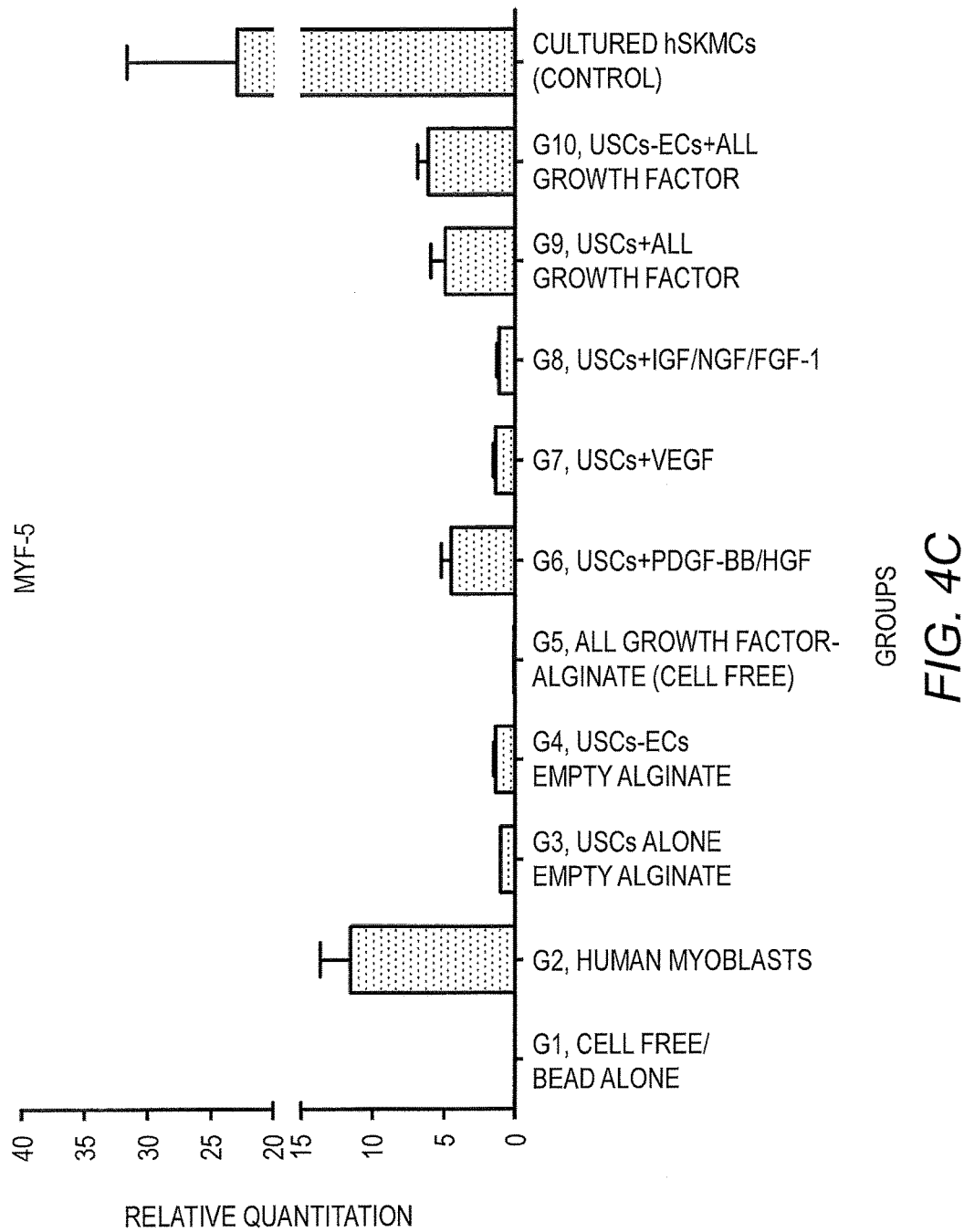

3.4.1 Myogenic differentiation of USCs. Expression of skeletal muscle-specific transcripts (Myo-D, desmin, and myf-5) were about 4-5-fold greater in USCs with myogenic growth factors (Group 6), all growth factors (Group 9), or plus ECs (Group 10) (FIGS. 4A-4C). The highest levels of the transcript were in cultured human skeletal muscle cells (control) and in the graft with skeletal muscle cell plus empty beads (Group 2), and there was no expression in the gel-alone group (Group 1). Immunofluorescent triple staining of myogenic markers, human nuclei, and DAPI showed that numbers of implanted cells expressing the skeletal muscle markers significantly increased in Groups 2, 9, and 10; the next was Group 6, consistent with real-time PCR data. Many cells without human nuclei expression also displayed myogenic markers in Groups 9-10, indicating that the resident cells migrated from the host into the graft tissue (FIGS. 4D-4F).

Figure 4D:
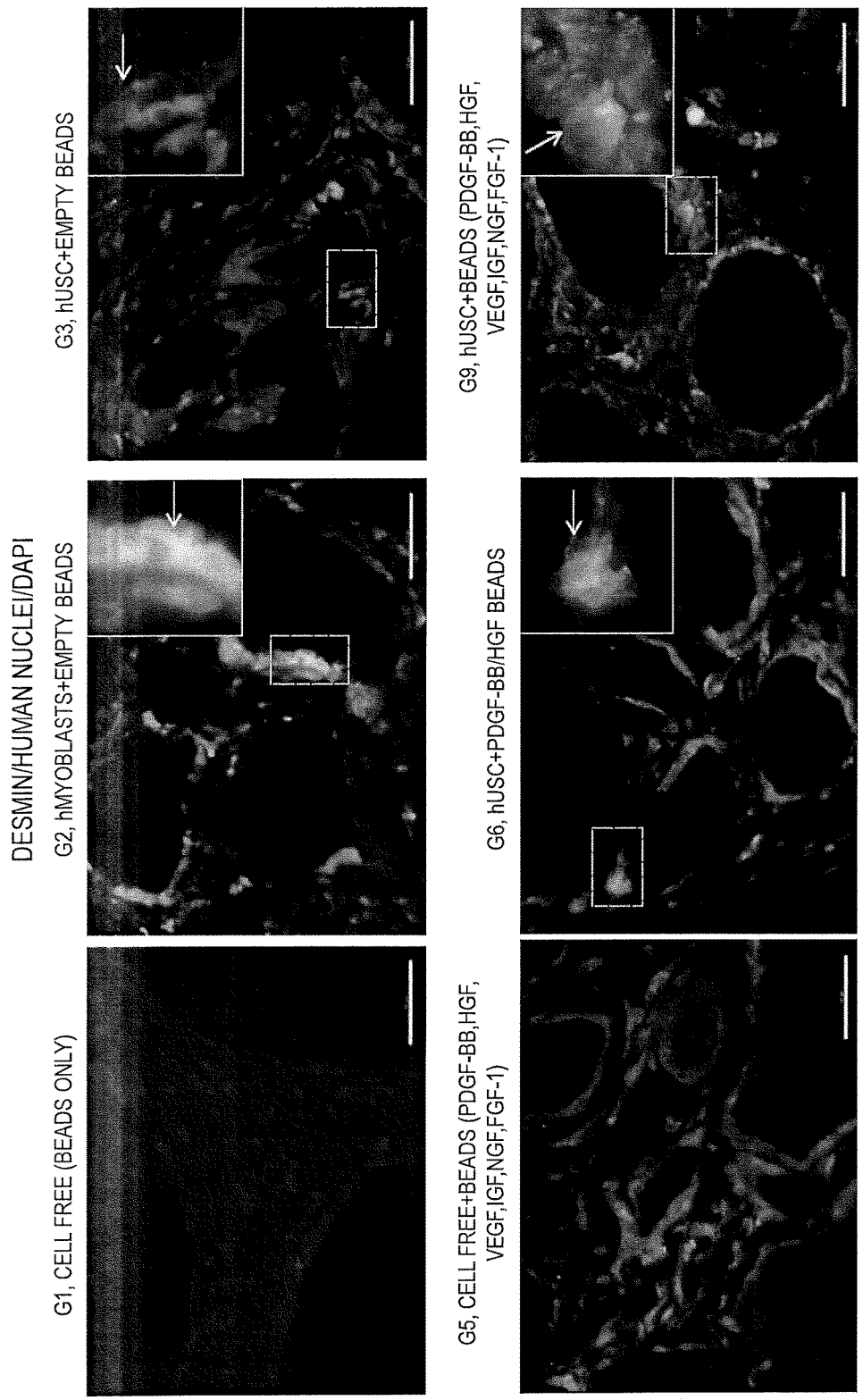
Figure 4E:
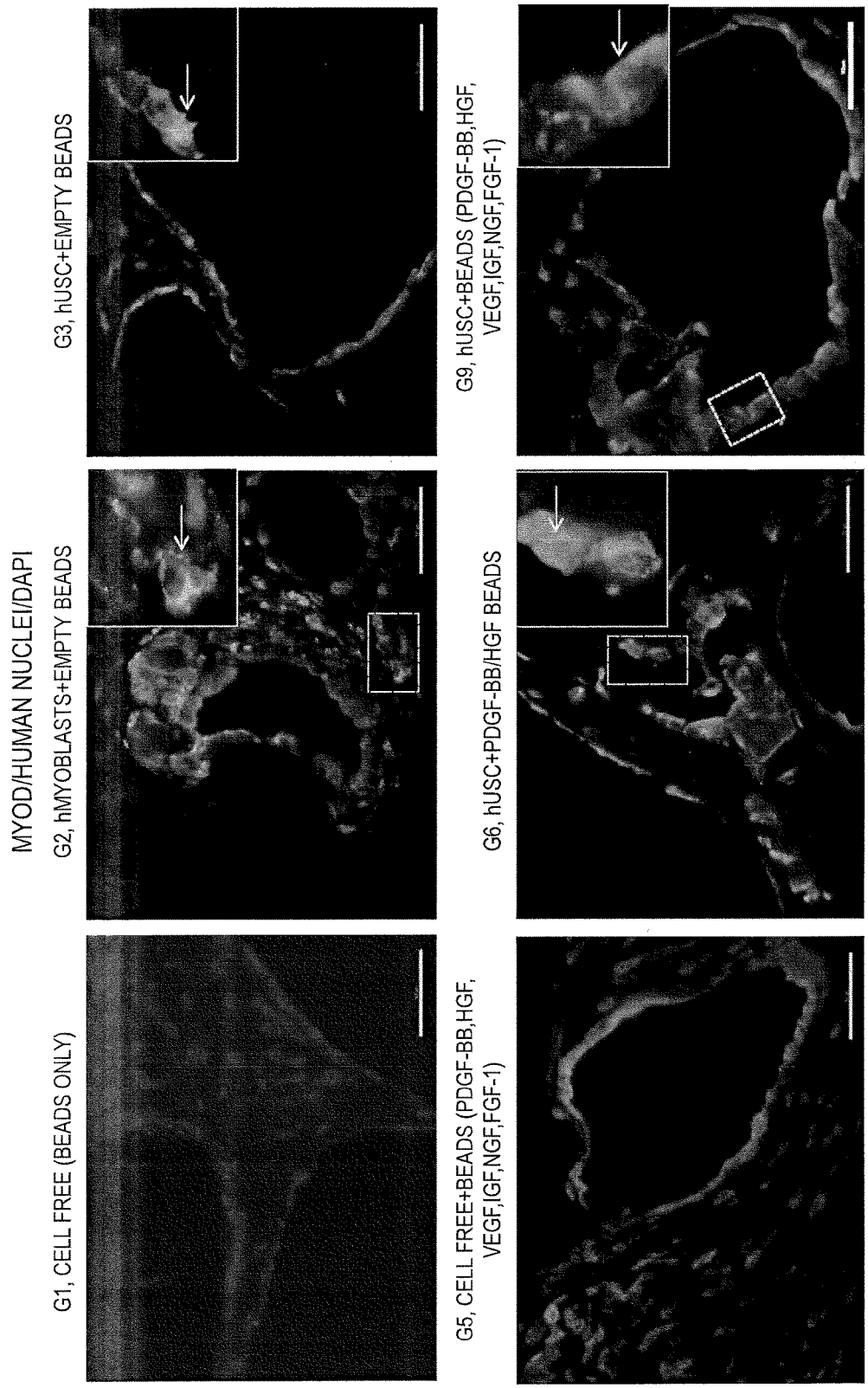
Figure 4F:
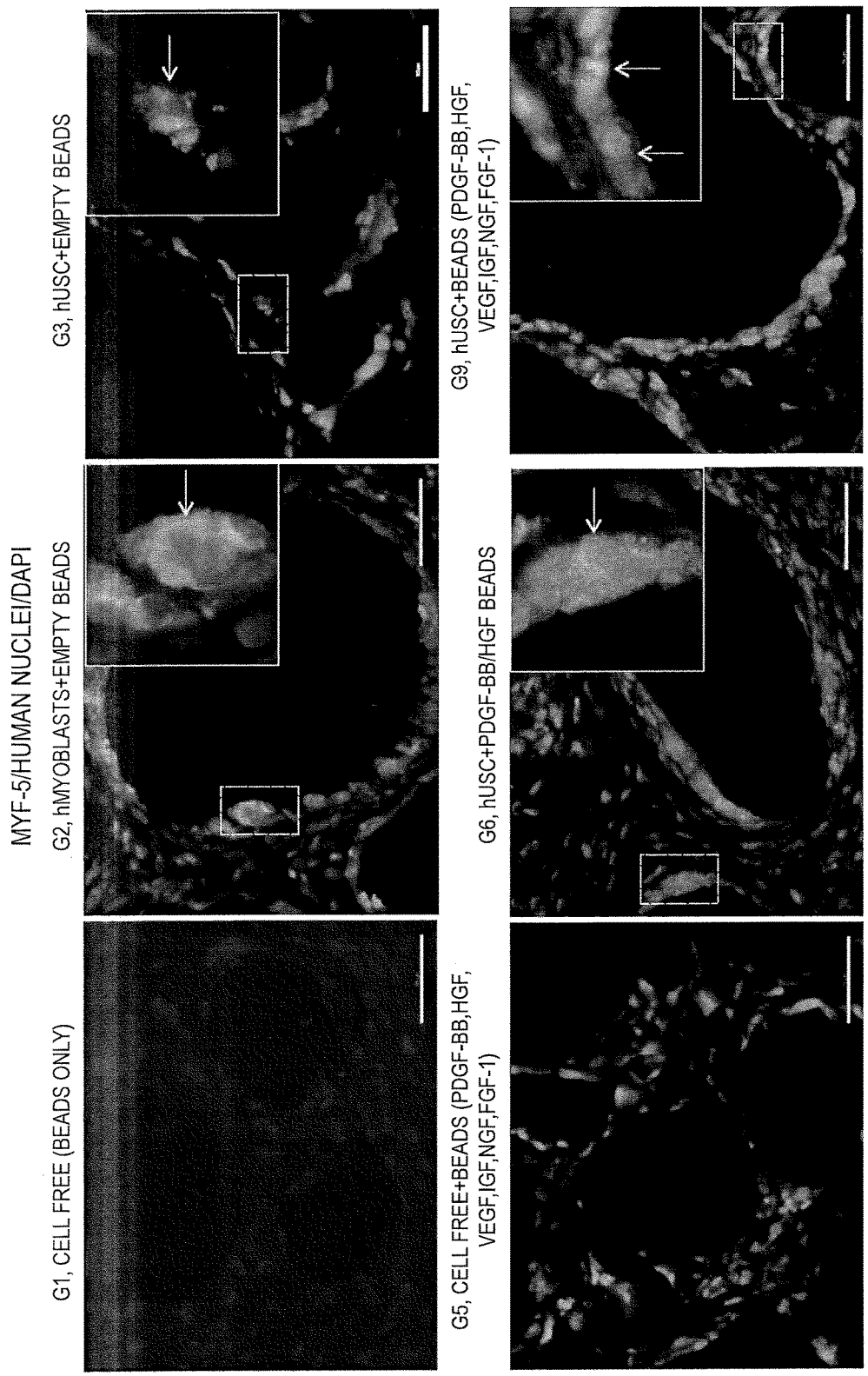

Interestingly, a few cells were positive for myogenic marker and human nuclei staining in the USC-alone group (Group 3), suggesting that some implanted USCs or growth factors could be induced to form skeletal muscle-like cells in vivo (FIGS. 4D-4F, Table 4). Furthermore, triple staining showed that some cells without human nuclei staining displayed myogenic marker expression in Groups 3-5, indicating that some resident cells gave rise to myocytes.

Figure 5A:
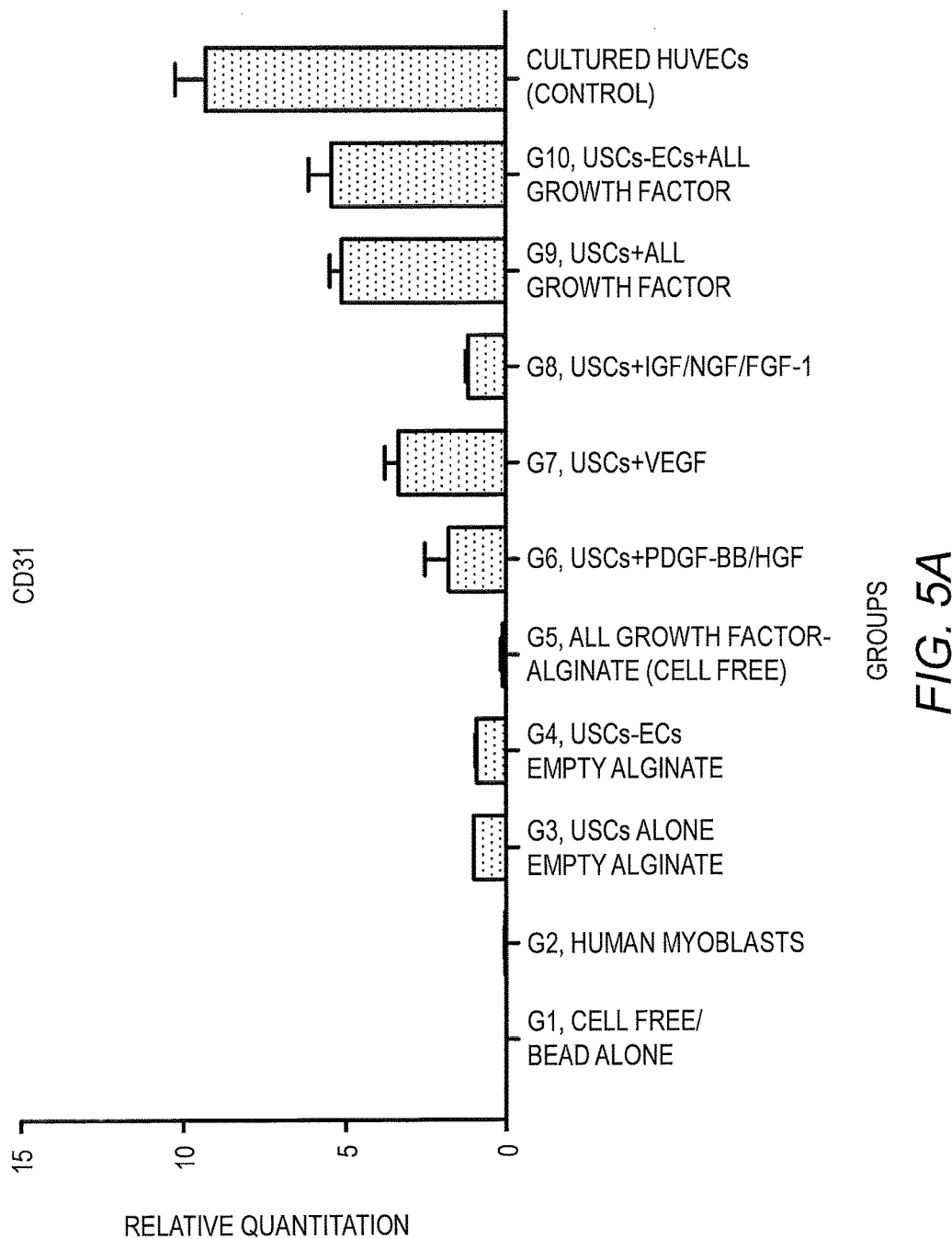
FIGS. 5A-5D. Endothelial differentiation of USCs and angiogenesis of implanted grafts 28 days after implantation in vivo. Quantitative real-time PCR was performed on total RNA from all groups using endothelial-specific primers (CD31 (FIG. 5A), vWF (FIG. 5B)). Groups 1, 3, 4, 5, 7, and 9 were subjected to immunofluorescent staining using the epithelial markers CD31 (FIG. 5C) and von Willebrand factor (vWF.
Figure 5B:
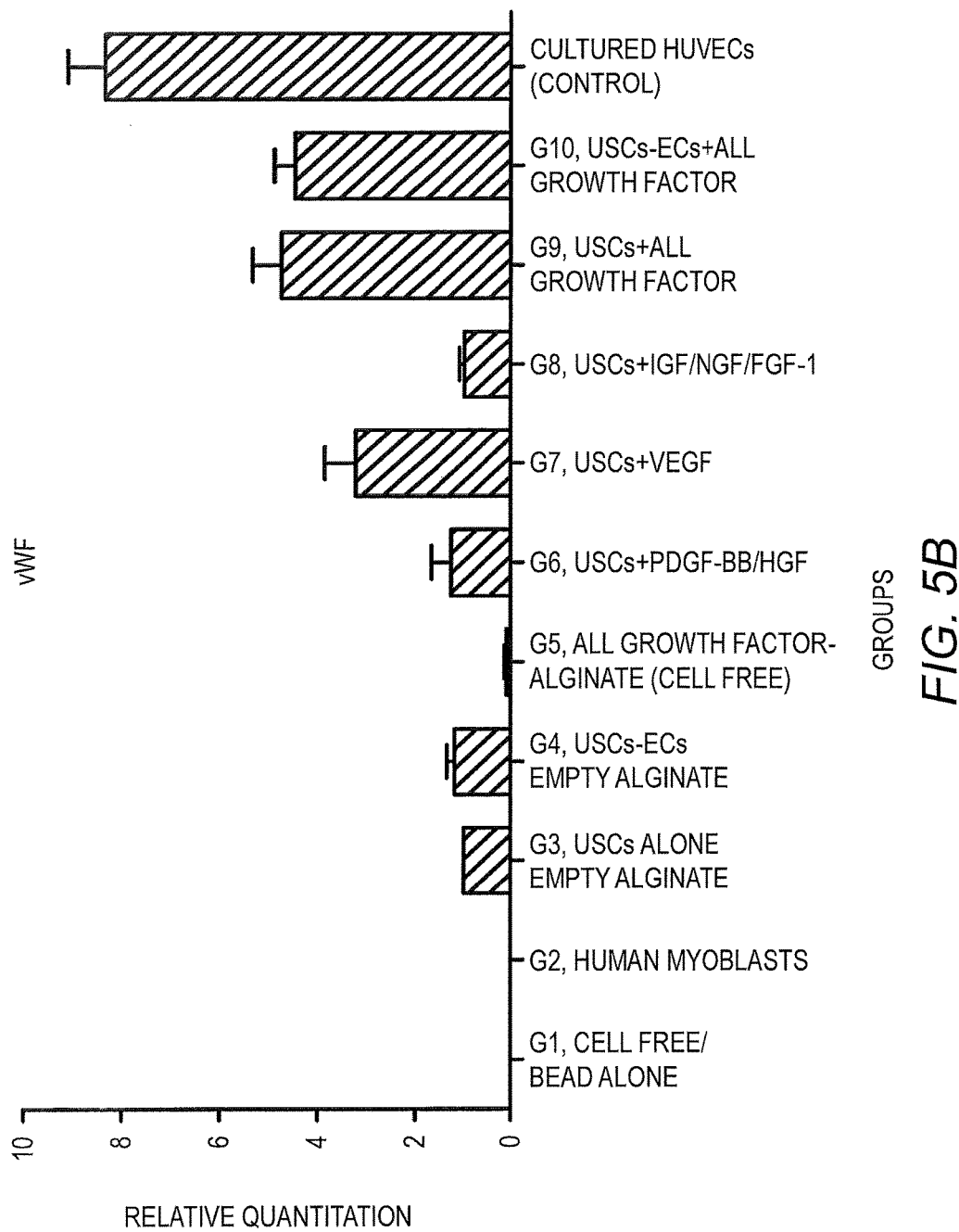

3.4.2 Angiogenesis and neo-vessel formation. Expression level of endothelial cell transcripts (CD31 and vWF) was significantly higher, in Groups 9 and 10, compared to the other groups (P<0.05) (FIGS. 5A-5B) except in the cultured HUVECs used as positive control. No significant differences in transcript expression were found between Groups 9 and 10. The same pattern was shown in triple staining. More cells around the microbeads were positive for endothelial cell markers compared to the cells further away from the beads. In addition, beside the cells with human nuclei expression, many cells without human nuclei expression were also positive for endothelial markers in all groups, suggesting that resident cells migrated from the host to participate in angiogenesis.

Figure 5C:
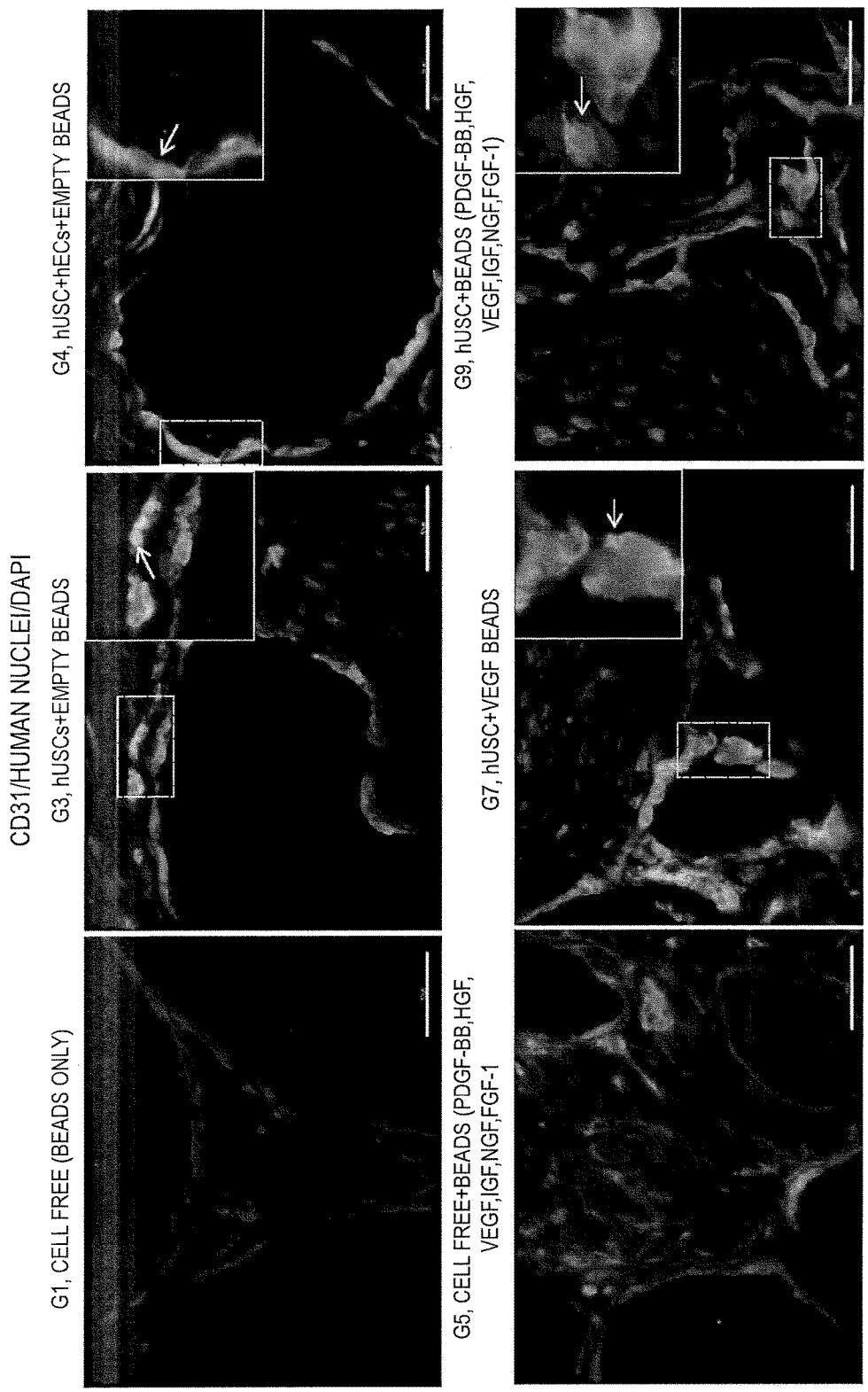
Figure 5D:
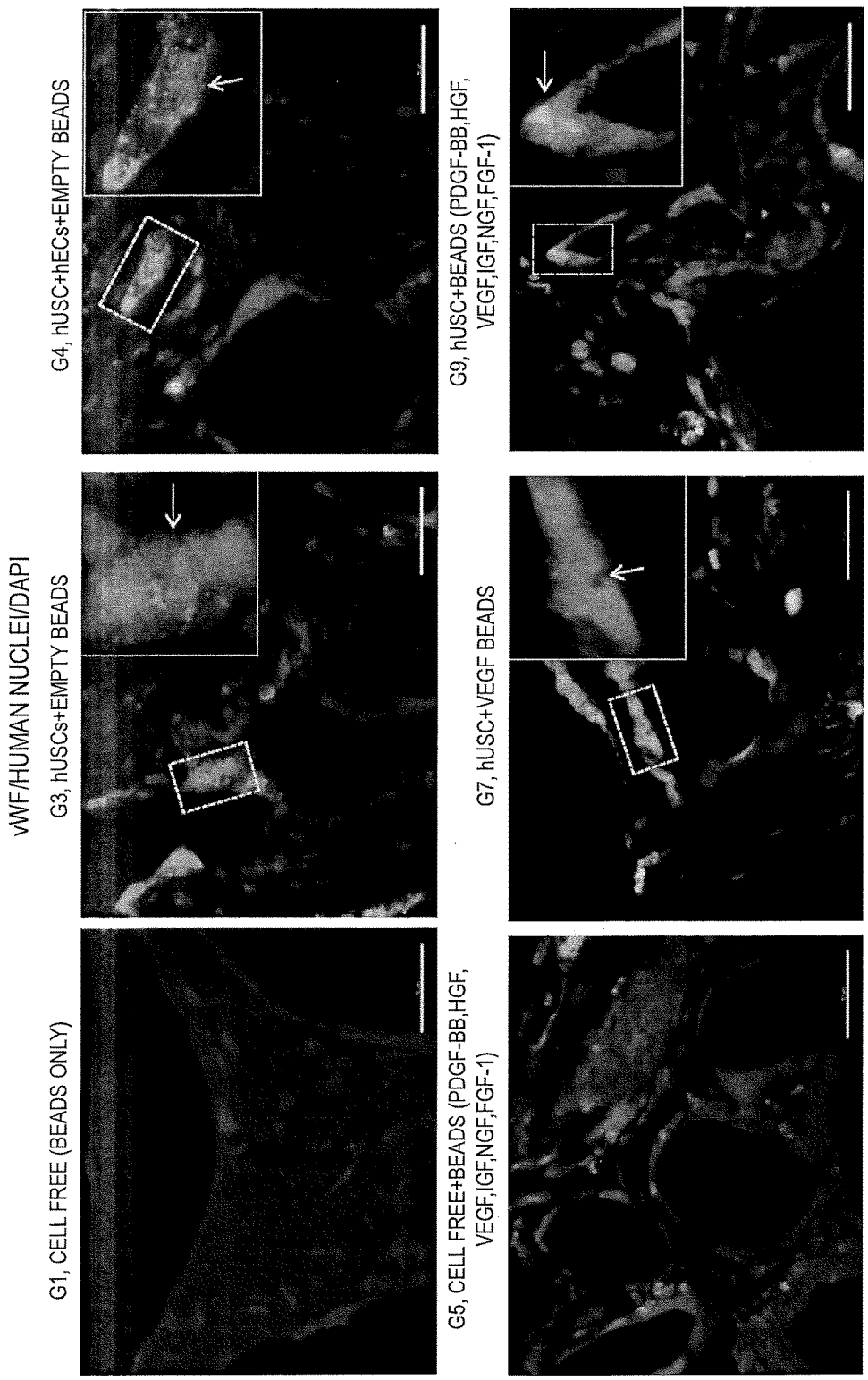

More cells were positive for endothelial cell markers and more neo-vessels formed in the groups with growth factors beads alone (Group 5) compared to the group with skeletal myocytes (Group 2) or gel alone (Group 1), indicating that growth factors induced angiogenesis from the host tissue (FIGS. 5C-5D, Table 4). Interestingly, a few cells in the USC-alone group (Group 3) were positive for both human nuclei and endothelial markers, implying that implanted USCs may participate in angiogenesis in vivo even without growth factor delivery.

Figure 6A:
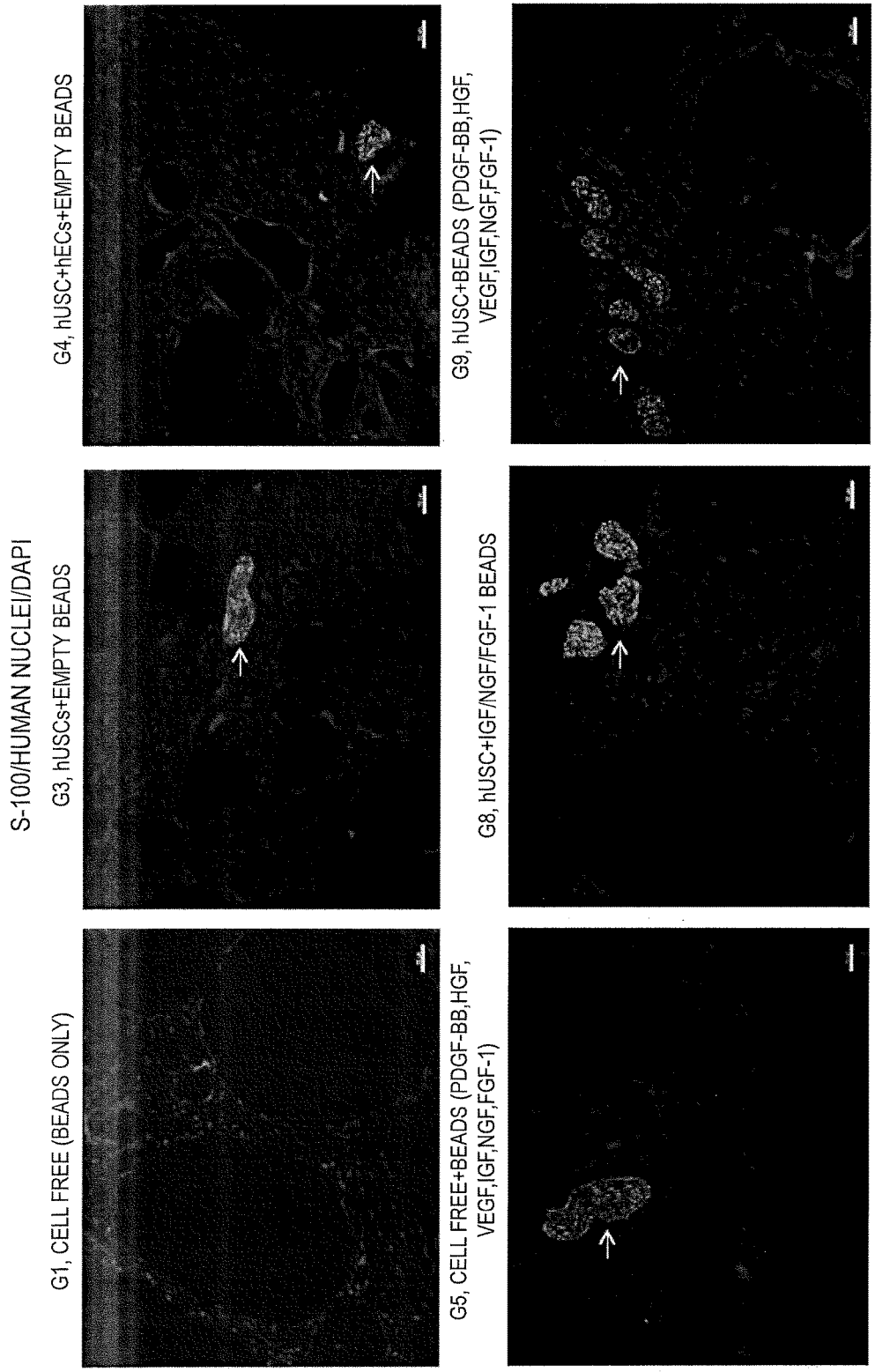
FIGS. 6A-6C. Innervation of implanted grafts 28 days after implantation. Cross-sections of samples from Groups 1, 3, 4, 5, 8, and 9 were subjected to immunofluorescent staining using DAPI (blue), human nuclear (red) and nerve cell antibodies (green)-S-100 (FIG. 6A) and Neurofilament (NF, FIG. 6B). Scale bar=50 μm. Semiquantitative analyses of nerve fibers in the implanted grafts (FIG. 6C).
Figure 6B:
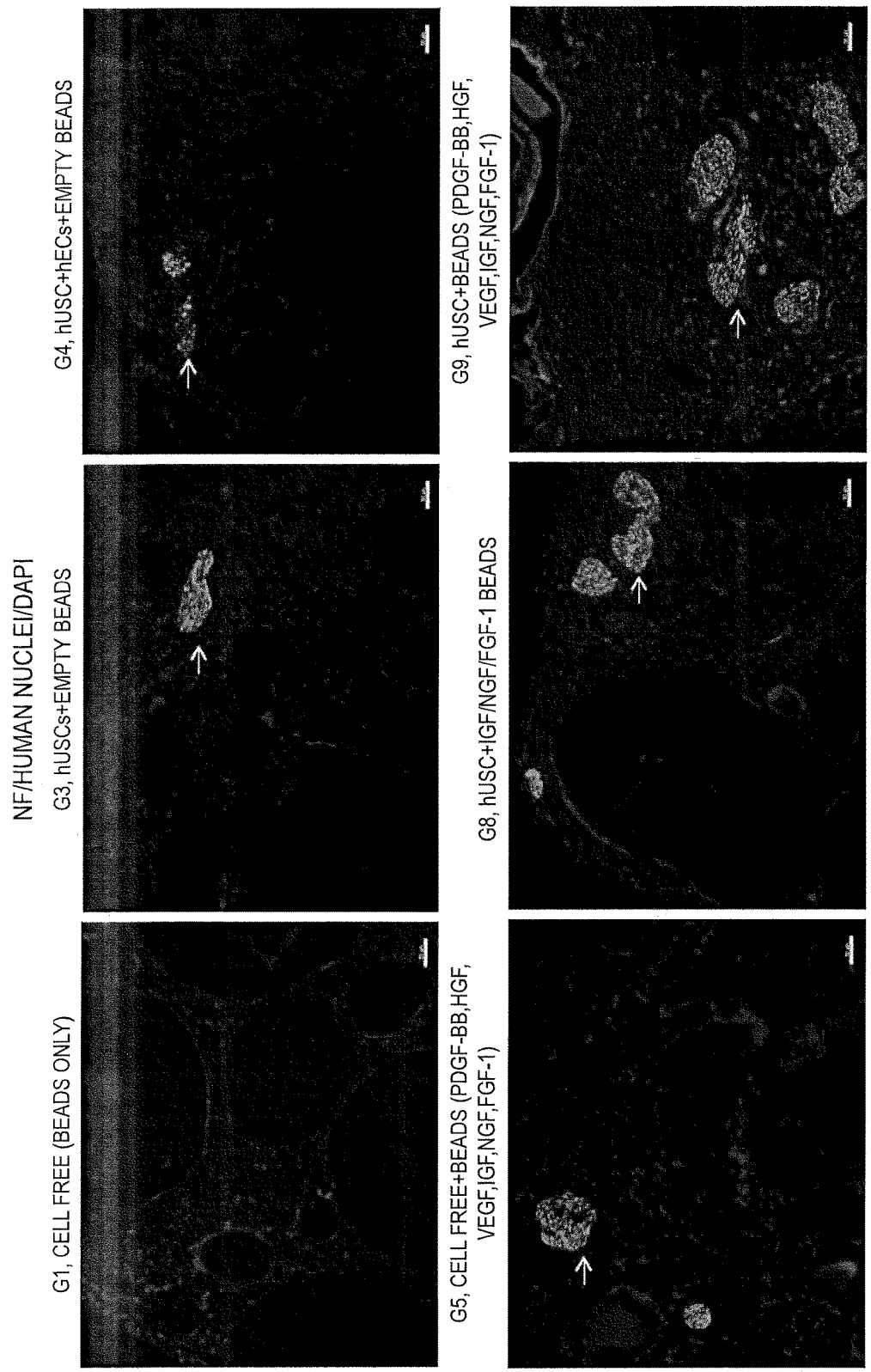
Figure 6C:
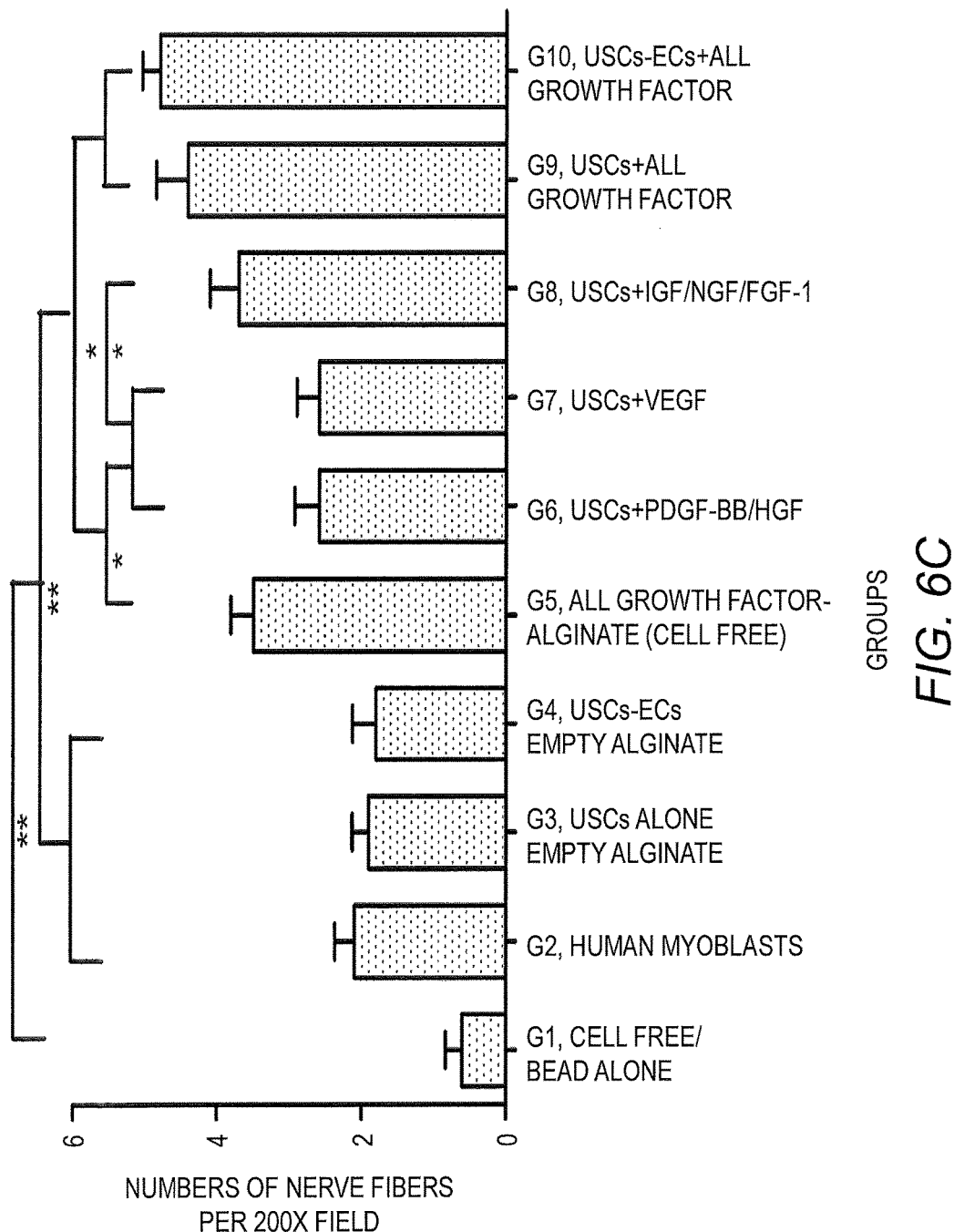

3.4.3 Innervation. Innervation was greater in Groups 9 and 10 as identified by semi-quantitative analysis with triple immunofluorescence staining (FIGS. 6A-6B), including peripheral nerve cell markers (neurofilament and S-100) combined with human nuclei and DAPI. The least amount of innervation was in the gel-alone group (FIG. 6C, Table 4). Most new nerve fibers were around the edges of grafts, but a few cells expressing human nuclear markers were found in new nerve fibers. In addition, microspheres loaded with all six growth factors without USCs (Group 5) showed a similar amount of innervation (FIG. 6C). These data could indicate that nerve fibers were derived from the host tissue, not the implanted cells.

Discussion

Two potential treatments have been investigated to accelerate tissue repair from sites of chronic injury or ischemia, growth factor therapy [33] and stem cell therapy. A new approach combining both therapies has been recently studied to induce stem cell differentiation and increase cell differentiation efficiency for tissue repair [34]. The present study documents a series of experiments aimed at demonstrating potential treatments for patients with SUI. Using a feasible delivery system with synergistic growth factors, we report that implanted autologous USCs were induced to differentiate into a myogenic lineage, and that the growth factor combinations enhanced angiogenesis and innervation, and stimulated resident cells to participate in regeneration of urethra sphincter tissue.

The sphincter muscle unit of the urethra has both internal and external sphincter muscles. The internal sphincter is the extension of the detrusor muscle (the primary muscle for forcing urine out of the bladder), is made of smooth muscle under involuntary or autonomic control. By contrast, the external sphincter is made of skeletal muscle under voluntary control of the somatic nervous system. Other connective tissues around the urethra, including vessels and peripheral nerves, also play important roles in control of micturition. Urinary incontinence may result from muscle weakness or injuries, nerve damage, or vascular (blood supply) changes, all of which are potential targets for stem cell therapies. Unlike using bulking materials to mechanically squeeze the urethra, a longer-term strategy to treat SUI is to repair defects of both skeletal and smooth muscle, and to improve the blood supply and innervation in the mid-urethral segment [35]. Several clinical trials have demonstrated that MSCs isolated from skeletal muscle or fat tissue injected into the middle urethra restored the damaged contractile function of the striated muscles and rhabdosphincter [36, 37]. The rationale of stem cell therapy is based on the multi-potent differentiation capability and trophic properties of these cells [38].

Stem cells can give rise to the target cells and secrete paracrine factors, such as angiogenic and cytoprotective factors, to prolong cell survival and facilitate vascularization. In the current study, USCs efficiently gave rise to skeletal myogenic or endothelial lineage cells in vivo via synergistic activity of growth factors released from microsphere vehicles. The growth factors not only improved the environment for the implanted cells by creating angiogenesis, they also recruited resident cells into the graft site for tissue repair. In addition, the combination of growth factors that facilitated myogenesis, angiogenesis, and innervation was more effective in in vivo tissue regeneration than the growth factors applied singly. Furthermore, this therapeutic approach would not require an initial step for in vitro stem cell differentiation, which shortens the process and increases cell differentiation efficiency.

An adequate blood supply is crucial for survival of cells in cell therapy, particularly in the central core of the implants [39, 40]. Our previous studies demonstrated that modifying USCs by exposing them to the angiogenic gene VEGF remarkably improved the cell survival rate and myogenic differentiation of USCs by promoting angiogenesis in vivo [18]. However, angiogenic gene manipulation causes potential side effects, such as extensive hemorrhaging within the liver [41] and tumorigenesis [42, 43] in implanted sites. Except for gene transfection, growth factor therapy including cytokines such as VEGF, HGF, IGF, NGF, PDGF, FGF, BMP, and EGF injections also acted as powerful therapeutic agents in tissue engineering [44]. However, most growth factors are soluble and disappear quickly due to their short half-life time in vivo. This approach also requires multiple injections of large doses of protein that results in several potential side effects, including only transient improvements [42] or abnormal vascular structure, resulting in insufficient therapeutic effect[44]. Thus, several growth factor delivery systems, such as chemical conjugation of the growth factor to the matrix, or physical encapsulation of growth factors in the delivery system [45], have been designed to overcome these disadvantages.

Different types of materials have been used to achieve cytokine or drug delivery, including biologics, polymers, silicon-based materials, carbon-based materials, or metals [46]. Among those delivery vehicles, alginate hydrogel microsphere beads are an excellent candidate for cytokine delivery, since they retain the bioactivity of the growth factors as cross-linking occurs under physiological conditions. The alginate microsphere beads can be optimized; higher concentrations of alginate yield a tightly cross-linked matrix, resulting in lower porosity and hence slower release of growth factors. Alginate-encapsulated proteins such as FGF-1[28], PDGF, and VEGF [47] have demonstrated a slow, low-level release of growth factors, and the efficacy of the delivery conduit was demonstrated both in vitro and in vivo. Unlike gene delivery or protein injection, the effective delivery of proteins, safety, and biocompatibility of microsphere beads provide promising benefits for angiogenesis [26-28].

Our previous study showed heparin binding to FGF-1 can increase its half-life and retain the normal mitogenic properties of FGF-1. Release time was prolonged when alginate microbeads were combined with the heparin-binding growth factors [48]. In the present study, single, two or multiple growth factors delivered from alginate microsphere beads significantly enhanced endothelial differentiation of USCs. Although some variation of release profile was noted when multiple growth factors were combined, they still retained constant-release properties. Differences may have resulted from growth factors of different molecular weights competing for release though the matrix. Our in vitro data confirmed that biologically active VEGF was released from the alginate microsphere beads, as assayed by endothelial differentiation of USC outgrowth induced by the VEGF-containing microsphere beads.

Increasing evidence has shown that cytokine combinations are better than a single cytokine in tissue repair [49]. In the present study, we investigated the impact of growth factors on angiogenesis with single, dual, or multiple delivery patterns in vivo. When given together, the growth factors had a synergistic effect that improved implanted cell survival, muscle tissue regeneration, neo-vacuolization, and innervations in vivo. Although IGF/NGF/FGF acts on innervation, VEGF on angiogenesis, and PDGF/HGF on myogenesis, most of them have cross-cutting properties. For example, PDGF not only induces myogenic differentiation of stem cells, but also promote angiogenesis[50]; furthermore, IGF can enhance innervation as well as promote myogenic differentiation of stem cells [51]. In addition, FGF-1 also promotes angiogenesis [26].

Grafts of USCs implanted with alginate microsphere beads containing neurogenic growth factors had more new nerve fibers, compared to the other experimental groups. The nerve fibers may have originated from the host tissue, rather than from the implanted USCs, because these regenerated nerve cells were largely not positive for few human nuclei staining. The present study also suggests that revascularization via angiogenic factors released from the microsphere beads enhanced both muscle regeneration and innervation in vivo.

In this study, we also demonstrated that USCs play an important role in cell survival, myogenesis, angiogenesis, innervation, and recruitment of resident cells. All groups of USCs with added growth factors achieved better outcomes than the groups with the same types of growth factors without USCs. Some USCs could give rise to endothelial cells without the addition of any growth factors, but these effects were strengthened by the presence of angiogenic growth factors in vivo. Interestingly, USCs alone (Group 9) and USCs with endothelial cells combined with angiogenic growth factors (Group 10) showed similar neo-vessel formation and myogenic regeneration, indicating that USCs could differentiate into endothelial cells. Therefore, endothelial differentiated USCs could replace endothelial cells with no necessity for adding extraneous endothelial cells to implanted grafts.

CONCLUSIONS

The present study has demonstrated that an alginate microsphere delivery system is feasible to control local levels of myogenic, anigogenic, and neurogenic growth factors and efficiently release multiple growth factors in vitro for over 4 weeks. The synergism of growth factors embedded in alginate microsphere beads can prolong grafted stem cell survival, promote myogenic differentiation of stem cells, enhance peripheral nerve regeneration, and recruit resident cells in vivo.

REFERENCES

[1] Sampselle C M, Miller J M, Mims B L, Delancey J O, Ashton-Miller J A, Antonakos C L. Effect of pelvic muscle exercise on transient incontinence during pregnancy and after birth. Obstet Gynecol. 1998; 91:406-12.

[2] Jemal A, Bray F, Center M M, Ferlay J, Ward E, Forman D. Global cancer statistics, CA: a cancer journal for clinicians. 2011; 61:69-90.

[3] Coelho R F, Rocco B, Patel M B, Orvieto M A, Chauhan S, Ficarra V, et al. Retropubic, laparoscopic, and robot-assisted radical prostatectomy: a critical review of outcomes reported by high-volume centers. J Endourol. 2010; 24:2003-15.

[4] Patel V R, Sivaraman A, Coelho R F, Chauhan S, Palmer K J, Orvieto M A, et al. Pentafecta: a new concept for reporting outcomes of robot-assisted laparoscopic radical prostatectomy. Eur Urol. 2011; 59:702-7.

[5] Wai C Y. Surgical treatment for stress and urge urinary incontinence. Obstet Gynecol Clin North Am. 2009; 36:509-19.

[6] Kim K, Taylor S L, Ganti S, Guo L, Osier M V, Weiss R H. Urine metabolomic analysis identifies potential biomarkers and pathogenic pathways in kidney cancer. Omics: a journal of integrative biology. 2011; 15:293-303.

[7] Attaran A, Boozary A. For peace and pain: the medical legitimisation of Afghanistan's poppy crop, Journal of epidemiology and community health. 2011; 65:396-8.

[8] Spector D, Deroo L A, Sandier D P. Lifestyle behaviors in black and white women with a family history of breast cancer. Preventive medicine. 2011; 52:394-7.

[9] Smith D P, Kaplan W E, Oyasu R. Evaluation of polydimethylsiloxane as an alternative in the endoscopic treatment of vesicoureteral reflux. J Urol. 1994; 152:1221-4.

[10] Chrouser K L, Fick F, Goel A, Itano N B, Sweat S D, Lightner D J. Carbon coated zirconium beads in beta-glucan gel and bovine glutaraldehyde cross-linked collagen injections for intrinsic sphincter deficiency: continence and satisfaction after extended follow up. J Urol. 2004; 171:1152-5.

[11] Eisinger F, Pivot X, Coscas Y, Viguier J, Calazel-Benque A, Blay J Y, et al. Impact of general practitioners' sex and age on systematic recommendation for cancer screening. Eur J Cancer Prev. 2011; 20 Suppl 1:S39-41.

[12] Harford J B, Otero I V, Anderson B O, Cazap E, Gradishar W J, Gralow J R, et al. Problem solving for breast health care delivery in low and middle resource countries (LMCs): consensus statement from the Breast Health Global Initiative. Breast. 2011; 20 Suppl 2:S20-9.

[13] Smith J S, Van Damme K, Randrianjafisamindrakotroka N, Ting J, Rabozakandraina T, Randrianasolo B S, et al. Human papillomavirus and cervical neoplasia among female sex workers in Madagascar. International journal of gynecological cancer: official journal of the International Gynecological Cancer Society. 2010; 20:1593-6.

[14] Menzies D. The case for a worldwide ban on smoking in public places. Current opinion in pulmonary medicine. 2011; 17:116-22.

[15] Sun Z, Asmann Y W, Kalari K R, Bot B, Eckel-Passow J E, Baker T R, et al. Integrated analysis of gene expression, CpG island methylation, and gene copy number in breast cancer cells by deep sequencing. PLoS One. 2011; 6:e17490.

[16] Rasu R S, Rianon N J, Shahidullah S M, Faisel A J, Selwyn B J. Effect of educational level on knowledge and use of breast cancer screening practices in Bangladeshi women. Health care for women international. 2011; 32:177-89.

[17] Steuerwald N M, Parsons J C, Bennett K, Bates T C, Bonkovsky H L. Parallel microRNA and mRNA expression profiling of (genotype 1b) human hepatoma cells expressing hepatitis C virus. Liver Int. 2010; 30:1490-504.

[18] Bharadwaj S, Liu G, Shi Y, Marked C, Andersson K E, Atala A, et al. Characterization of urine-derived stem cells obtained from upper urinary tract for use in cell-based urological tissue engineering. Tissue Eng Part A. 2011; 17:2123-32.

[19] Bodin A, Bharadwaj S, Wu S, Gatenholm P, Atala A, Zhang Y. Tissue-engineered conduit using urine-derived stem cells seeded bacterial cellulose polymer in urinary reconstruction and diversion. Biomaterials. 2010; 31:8889-901.

[20] Wu S, Liu Y, Bharadwaj S, Atala A, Zhang Y. Human urine-derived stem cells seeded in a modified 3D porous small intestinal submucosa scaffold for urethral tissue engineering. Biomaterials. 2011; 32:1317-26.

[21] Wu S, Wang Z, Bharadwaj S, Hodges S J, Atala A, Zhang Y Implantation of autologous urine derived stem cells expressing vascular endothelial growth factor for potential use in genitourinary reconstruction. J Urol. 2011; 186:640-7.

[22] Zhang Y, McNeill E, Tian H, Soker S, Andersson K E, Yoo J J, et al. Urine derived cells are a potential source for urological tissue reconstruction. J Urol. 2008; 180:2226-33.

[23] Urano M, Koike S, Ohara K. Secondary malignant neoplasms following radiotherapy of a mouse mammary carcinoma. Cancer. 1979; 43:151-6.

[24] Carpenter W R, Yeh W S, Wobker S E, Godley P A. Getting cancer prevalence right: using state cancer registry data to estimate cancer survivors. Cancer causes & control: CCC. 2011; 22:765-73.

[25] Haugaa K H, Bergestuen D S, Sahakyan L G, Skulstad H, Aakhus S, Thiis-Evensen E, et al. Evaluation of right ventricular dysfunction by myocardial strain echocardiography in patients with intestinal carcinoid disease. Journal of the American Society of Echocardiography: official publication of the American Society of Echocardiography. 2011; 24:644-50.

[26] Jung K, Becker B, Brunner E, Beissbarth T. Comparison of global tests for functional gene sets in two-group designs and selection of potentially effect-causing genes. Bioinformatics. 2011; 27:1377-83.

[27] Clemens K E, Quednau I, Klaschik E. Bowel function during pain therapy with oxycodone/naloxone prolonged-release tablets in patients with advanced cancer. International journal of clinical practice. 2011; 65:472-8.

[28] Oliva E N, Nobile F, Alimena G, Ronco F, Specchia G, Impera S, et al. Quality of life in elderly patients with acute myeloid leukemia: patients may be more accurate than physicians. Haematologica. 2011; 96:696-702.

[29] Harding R, Selman L, Agupio G, Dinat N, Downing J, Gwyther L, et al. The prevalence and burden of symptoms amongst cancer patients attending palliative care in two African countries. Eur J Cancer. 2011; 47:51-6.

[30] Hurmuzlu M, Aarstad H J, Aarstad A K, Hjermstad M J, Viste A. Health-related quality of life in long-term survivors after high-dose chemoradiotherapy followed by surgery in esophageal cancer. Dis Esophagus. 2011; 24:39-47.

[31] Sucheston L, Witonsky D B, Hastings D, Yildiz O, Clark V J, Di Rienzo A, et al. Natural selection and functional genetic variation in the p53 pathway. Human molecular genetics. 2011; 20:1502-8.

[32] Bharadwaj S, Wu S, Hodges S, Atala A, Zhang Y. Skeletal muscle differentiation of human urine-derived stem cells for injection therapy in the treatment of stress urinary incontinence. J Urology. 2011; 184:E681.

[33] Nekolaichuk C L, Cumming C, Turner J, Yushchyshyn A, Sela R. Referral patterns and psychosocial distress in cancer patients accessing a psycho-oncology counselling service. Psycho-oncology. 2011; 20:326-32.

[34] Leone L A, James A S, Allicock M, Campbell M K. Obesity predicts differential response to cancer prevention interventions among African Americans. Health education & behavior: the official publication of the Society for Public Health Education. 2010; 37:913-25.

[35] Bellino S, Fenocchio M, Zizza M, Rocca G, Bogetti P, Bogetto F. Quality of life of patients who undergo breast reconstruction after mastectomy: effects of personality characteristics. Plast Reconstr Surg. 2011; 127:10-7.

[36] Becker C, Jakse G. Stem cells for regeneration of urological structures. Eur Urol. 2007; 51:1217-28.

[37] Mitterberger M, Pinggera G M, Marksteiner R, Margreiter E, Fussenegger M, Frauscher F, et al. Adult stem cell therapy of female stress urinary incontinence. Eur Urol. 2008; 53:169-75.

[38] Tsai P J. Spatial autocorrelation calculations of the nine malignant neoplasms in Taiwan in 2005-2009: a gender comparison study. Chinese journal of cancer. 2011; 30:757-65.

[39] Mordukhovich I, Reiter P L, Backes D M, Family L, McCullough L E, O'Brien K M, et al. A review of African American-white differences in risk factors for cancer: prostate cancer. Cancer causes & control: CCC. 2011; 22:341-57.

[40] Carter J, Raviv L, Sonoda Y, Chi D S, Abu-Rustum N R. Recovery issues of fertility-preserving surgery in patients with early-stage cervical cancer and a model for survivorship: the physician checklist. International journal of gynecological cancer: official journal of the International Gynecological Cancer Society. 2011; 21:106-16.

[41] Montoya J E, Domingo F, Jr., Luna C A, Berroya R M, Catli C A, Ginete J K, et al. Nutritional status of cancer patients admitted for chemotherapy at the National Kidney and Transplant Institute. Singapore medical journal. 2010; 51:860-4.

[42] Djary T, Lagergren P. Six-month postoperative quality of life predicts long-term survival after oesophageal cancer surgery. Eur J Cancer. 2011; 47:530-5.

[43] Daniel C R, Cross A J, Koebnick C, Sinha R. Trends in meat consumption in the USA. Public health nutrition. 2011; 14:575-83.

[44] Brocklehurst P, Kujan O, Glenny A M, Oliver R, Sloan P, Ogden G, et al. Screening programmes for the early detection and prevention of oral cancer. Cochrane Database Syst Rev. 2010: CD004150.

[45] Murthy N S, Nandakumar B S, Pruthvish S, George P S, Mathew A. Disability adjusted life years for cancer patients in India. Asian Pacific journal of cancer prevention: APJCP. 2010; 11:633-40.

[46] Mok T, Wu Y L, Au J S, Zhou C, Zhang L, Perng R P, et al. Efficacy and safety of erlotinib in 1242 East/South-East Asian patients with advanced non-small cell lung cancer. Journal of thoracic oncology: official publication of the International Association for the Study of Lung Cancer. 2010; 5:1609-15.

[47] Garcia Cabezas S, Palacios Eito A, Martinez Paredes M, Rivin del Campo E. Radiotherapy in rectal cancer: development, adequacy and radiotherapy utilisation rate. A comparative analysis with the most frequent tumour sites. Clinical & translational oncology: official publication of the Federation of Spanish Oncology Societies and of the National Cancer Institute of Mexico. 2011; 13:115-20.

[48] de Lavallade H, Garland P, Sekine T, Hoschler K, Marin D, Stringaris K, et al. Repeated vaccination is required to optimize seroprotection against H1N1 in the immunocompromised host. Haematologica. 2011; 96:307-14.

[49] Banning M. Perceptions of breast health awareness in Black British women. European journal of oncology nursing: the official journal of European Oncology Nursing Society. 2011; 15:173-7.

[50] Wu F, Sun P R, Chang C C. Apply influence diagrams for utility analysis of paying the weight-reducing expenses: a case study in taiwan. Journal of medical systems. 2011; 35:105-11.

[51] Wang N, Gerling G J, Krupski T L, Childress R M, Martin M L. Using a prostate exam simulator to decipher palpation techniques that facilitate the detection of abnormalities near clinical limits. Simulation in healthcare: journal of the Society for Simulation in Healthcare. 2010; 5:152-60.

TABLE 1

Research Design

| Groups (G) | Function groups | Injections of Cell-Microsphere Beads in Collagen I gel | Doses of growth factors/injection | Number of Grafts/Number of Animals |
|---|---|---|---|---|
| G1 | Control 1 | Cell-free/empty beads | 0 | 8/2 |
| G2 | Control 2 | Human Myoblasts/empty beads | 0 | 8/2 |
| G3 | Control 3 | USCs/empty beads | 0 | 8/2 |
| G4 | Control 4 | USCs-EC/empty beads | 0 | 8/2 |
| G5 | Control 5 | Cell-free combine with IGF/NGF/FGF-1 + VEGF + PDGF/HGF beads | IGF (43.75 ng), NGF(7.8 ng), FGF-1(15.625 ng), VEGF (21.875 ng), PDGF-BB (12.5 ng), HGF (62.5 ng) | 8/2 |
| G6 | Myogenic | USCs combine with PDGF-BB/HGF beads | PDGF-BB (37.5 ng), HGF (187.5 ng) | 8/2 |
| G7 | Angiogenic | USCs combine with VEGF beads | VEGF (65.6 ng) | 8/2 |
| G8 | Neurogenic | USCs combine with IGF/NGF/FGF-1 beads | IGF (131.25 ng), NGF(23.44 ng), FGF-1(46.875 ng) | 8/2 |
| G9 | Synergetic 1 | USCs combine with IGF/NGF/FGF-1 + VEGF + PDGF/HGF beads | IGF (43.75 ng), NGF(7.8 ng), FGF-1(15.625 ng), VEGF (21.875 ng), PDGF-BB (12.5 ng), HGF (62.5 ng) | 16/4 |
| G10 | Synergetic 2 | USCs-ECs combine with IGF/IMGF/FGF-1 + VEGF + PDGF/HGF beads | IGF (43.75 ng), NGF(7.8 ng), FGF-1(15.625 ng), VEGF (21.875 ng), PDGF-BB (12.5 ng), HGF (62.5 ng) | 16/4 |

TABLE 2

Antibodies used in this study

| Cell markers | | Host | Dilution | Company |
|---|---|---|---|---|
| CD31 | Endothelial cells | Goat | 1:100 | Santa Cruz SC-1506 |
| vWF | Endothelial cells | Rab | 1:200 | Dako A0086 |
| Desmin | Skeletal muscle cells | Goat | 1:100 | Santa Cruz SC-7559 |
| Myf-5 | Skeletal muscle cells | Goat | 1:100 | Santa Cruz SC-12117 |
| Myo D | Skeletal muscle cells | Rab | 1:100 | Santa Cruz SC-304 |
| Human nuclei | Human nuclear | Mouse | 1:50 | Millipore MAB1281 |
| S-100 | Peripheral nerve | Rab | 1:100 | Abcam ab868 |
| GFAP | Schwann cells | Rab | 1:1000 | Abcam ab7779 |
| NF | Peripheral nerve | Rab | 1:1000 | Primary antibody |

TABLE 3

Primers for real-time PCR used in this study*

| Primary antibody | Cell markers | Catalog # |
|---|---|---|
| CD31 | Endothelial cells | Hs01065279_m1 |
| vWF | Endothelial cells | Hs00169795_m1 |
| Desmin | Skeletal muscle cells | Hs01090875 |
| Myf-5 | Skeletal muscle cells | Hs00224610 |
| MyoD | Skeletal muscle cells | Hs00159528_m1 |
| GAPDH | Housekeeping gene | NM_002046.3 |

*All primers obtained from Applied Biosystems, Foster City, CA.

TABLE 4

Summary of USC subcutaneous injection in vivo for 28 days

| | Groups | | | | | | | | | |
|---|---|---|---|---|---|---|---|---|---|---|
| | 1<br>Cell-free +<br>empty<br>beads | 2<br>Human<br>Myoblasts +<br>empty<br>beads | 3<br>USC +<br>empty<br>beads | 4<br>USC/EC +<br>empty<br>beads | 5<br>Cell<br>free + all<br>growth factor<br>beads | 6<br>USC +<br>PDGF/HGF<br>beads | 7<br>USC +<br>VEGF<br>Beads | 8<br>USC +<br>IGF/<br>FGF/NGF<br>Beads | 9<br>USC + All<br>growth factor<br>containing<br>beads | 10<br>USC/EC + All<br>growth factor<br>containing<br>beads |
| Gross measurement | | | | | | | | | | |
| Graft size | 2+ | 3+~4+ | 3+ | 3+ | 3+ | 4+ | 3+~4+ | 4+ | 3+~4+ | 4+ |
| Blood supply | − | +~2+ | 2+ | 2+ | 2+~3+ | 3+ | 3+~4+ | 2+~3+ | 4+ | 4+ |
| Cell density | | | | | | | | | | |
| DAPI staining | + | 3+~4+ | 2+~3+ | 2+~3+ | 2+ | 3+ | 4+ | 3+~4+ | 4+ | 4+ |
| Human nuclei staining | − | 3+ | 2+ | 2+~3+ | − | 3+ | 3+~4+ | 3+ | 3+~4+ | 4+ |
| Muscle regeneration | | | | | | | | | | |
| MyoD | −~+ | 3+~4+ | 2+ | 2+ | 2+ | 3+~4+ | 3+ | 2+~3+ | 3+~4+ | 4+ |
| Desmin | − | 4+ | 2+ | +~2+ | 2+ | 4+ | 2+~3+ | 3+ | 4+ | 4+ |
| Myf-5 | − | 4+ | +~2+ | 2+ | 2+~3+ | 3+ | 2+~3+ | 2+ | 3+~4+ | 4+ |
| Angiogenesis | | | | | | | | | | |
| Trichorome observation | + | 2+~3+ | 2+ | 2+ | +~2+ | 3+ | 3+~4+ | 3+ | 4+ | 4+ |
| CD 31 | −~+ | 2+ | 2+~3+ | 2+ | 2+~3+ | 3+ | 3+~4+ | 3+ | 3+~4+ | 4+ |
| vWF | −~+ | +~2+ | 2+ | 2+~3+ | 2+~3+ | 2+~3+ | 3+ | 3+ | 4+ | 4+ |
| Nerve regeneration | | | | | | | | | | |
| S-100 | −~+ | +~2+ | +~2+ | + | 2+ | +~2+ | 2+ | 3+ | 4+ | 4+ |
| NF | −~+ | 2+ | 2+ | +~2+ | 2+ | 2+ | 2+~3+ | 3+~4+ | 3+~4+ | 4+ |

Notes:
All growth factors including PDGF-BB/HGF/VEGF/IGF/FGF-1/NGF.
− no targeted cell or capillary;
+ 1%-25% of G10 changes;
++ 25%-50% of G10 changes;
+++ 50%-75% of G10 changes;
++++ G10 changes as standard The foregoing is illustrative of the present invention, and is not to be construed as limiting thereof. The invention is defined by the following claims, with equivalents of the claimed to be included therein.

That which is claimed is:

1. A method of treating stress urinary incontinence or vesicoureteral reflux in a subject in need thereof, comprising:
    administering urine stem cells to the urethra of said subject in a treatment effective amount; and, in conjunction therewith,
    administering growth factors to said subject in an amount effective to promote differentiation of said stem cells into skeletal muscle cells,
    wherein said growth factors comprise an angiogenic growth factor, a skeletal myogenic growth factor, and a neurogenic growth factor, and wherein said growth factors are selected from the group consisting of VEGF, IGF-1, FGF-1, PDGF, HGF, and NGF.

2. The method of claim 1, wherein said administering is carried out by injection.

3. The method of claim 1, wherein said administering is carried out by injection into a sphincter muscle tissue.

4. The method of claim 1, wherein said growth factors are provided in a polymeric matrix.

5. The method of claim 1, wherein said growth factors are provided in polymeric microspheres.

6. The method of claim 5, wherein said polymeric microspheres comprise alginate.

7. The method of claim 1, wherein said growth factors are released over a period of from 2 to 6 weeks.

8. The method of claim 1, wherein said cells are provided in a pharmaceutically acceptable carrier.

9. The method of claim 8, wherein said carrier comprises a collagen gel, a hydrogel, a temperature sensitive gel or a hyaluronic acid gel.

10. The method of claim 1, wherein said administering is carried out by simultaneous administration of said cells and said growth factors.

11. The method of claim 10, wherein said cells and said growth factors are provided in the same composition for said administering.

12. The method of claim 1, wherein said subject is in need of treatment for stress urinary incontinence.

13. The method of claim 1, wherein said growth factors comprise IGF-1.

* * * * *